United States Patent [19]

Wang et al.

[11] Patent Number: 5,541,072
[45] Date of Patent: Jul. 30, 1996

[54] METHOD FOR MAGNETIC SEPARATION FEATURING MAGNETIC PARTICLES IN A MULTI-PHASE SYSTEM

[75] Inventors: Yuzhou Wang, Wayne; Weixin Tang, Landsdale, both of Pa.; William J. Cronin, Matawan, N.J.; Paul A. Liberti, Huntingdon Valley, Pa.

[73] Assignee: Immunivest Corporation, Wilmington, Del.

[21] Appl. No.: 228,818

[22] Filed: Apr. 18, 1994

[51] Int. Cl.$^6$ .................... G01N 33/567; G01N 33/569
[52] U.S. Cl. ................ 435/7.21; 209/214; 209/223.1; 210/695; 210/222; 210/767; 435/2; 435/5; 435/6; 435/7.1; 435/7.23; 435/7.31; 435/7.32; 436/501; 436/518; 436/526; 436/807; 436/824; 436/177
[58] Field of Search .................. 422/58, 101; 209/214, 209/223.1; 210/695, 222, 767; 435/2, 4, 5, 6, 7.1, 7.2, 7.21, 7.23, 7.31, 7.32; 436/501, 518, 526, 807, 824, 174, 177

[56] References Cited

U.S. PATENT DOCUMENTS

| | | | |
|---|---|---|---|
| 3,326,374 | 6/1967 | Jones | 209/214 |
| 3,402,820 | 9/1968 | Lohmann | 210/222 |
| 3,608,718 | 9/1971 | Aubrey, Jr. et al. | 209/214 |
| 3,985,649 | 10/1976 | Eddelman | 210/695 |
| 4,018,886 | 4/1977 | Giaever | 436/526 |
| 4,141,687 | 2/1979 | Forrest et al. | 436/526 |
| 4,230,685 | 10/1980 | Senyei et al. | 436/526 |
| 4,498,987 | 2/1985 | Inaba | 210/222 |
| 4,659,678 | 4/1987 | Forrest et al. | 436/512 |
| 4,663,029 | 5/1987 | Keiland et al. | 209/214 |
| 4,672,040 | 6/1987 | Josephson | 436/526 |
| 4,714,680 | 12/1987 | Civin | 435/317.1 |
| 4,895,650 | 1/1990 | Wang | 210/222 |
| 4,904,391 | 2/1990 | Freeman | 210/695 |
| 4,910,148 | 3/1990 | Sorensen et al. | |
| 4,935,147 | 6/1990 | Ullman et al. | 210/695 |

(List continued on next page.)

FOREIGN PATENT DOCUMENTS

| | | |
|---|---|---|
| A229488 | 4/1989 | Australia . |
| 0030087 | 6/1981 | European Pat. Off. . |
| 0149565 | 7/1985 | European Pat. Off. . |
| 0230768 | 8/1987 | European Pat. Off. . |
| WO91/16452 | of 0000 | WIPO . |
| WO90/07380 | 4/1990 | WIPO . |
| WO91/09938 | 4/1991 | WIPO . |

OTHER PUBLICATIONS

Owen, C. S. et al., *Cell Separation Methods and Selected Applications*, vol. 4, Academic Press, Inc., New York, Pretlowet Al., Ebs., "Magnetite–Protein Conjugates for the Separation of Cells by High Gradient Magnetic Filtration" (1987) pp. 259–275.

(List continued on next page.)

Primary Examiner—Lila Feisee
Assistant Examiner—Susan C. Wolski
Attorney, Agent, or Firm—Dann, Dorfman, Herrell and Skillman

[57] ABSTRACT

Methods and devices are provided for separation of magnetic particles and/or magnetic-associated substances from non-magnetic associated substances and media. The methods are specifically applicable to biological separation, and utilize a phase phenomenon arising from mutual interactions between suspended magnetic particles and interactions with the suspension medium. The phenomenon is exploited to produce and maintain a distinct, structured phase of magnetic particles, or ferrophase, within a multi-phase liquid system. A ferrophase is established within a separation chamber prior to introducing therein a test sample containing the target substances to be separated. The formation of a ferrophase is used to transport target substances from regions of relatively low magnetic field gradient to regions of relatively high magnetic field gradient within a high-gradient magnetic separation apparatus. Such transport of the ferrophase is accomplished at greater speed than the transport of individual magnetic particles within a single liquid phase, thereby enabling a more effective separation of magnetic from non-magnetic components.

39 Claims, 5 Drawing Sheets

U.S. PATENT DOCUMENTS

| | | | |
|---|---|---|---|
| 4,946,590 | 8/1990 | Hertzog | 210/222 |
| 4,988,618 | 1/1991 | Li et al. | 435/6 |
| 5,061,620 | 10/1991 | Tsukamoto et al. | 435/7.21 |
| 5,108,933 | 4/1992 | Liberti et al. | 436/501 |
| 5,186,827 | 2/1993 | Liberti et al. | 210/222 |
| 5,200,084 | 4/1993 | Liberti et al. | 210/695 |
| 5,466,574 | 11/1995 | Liberti et al. | 435/5 |

OTHER PUBLICATIONS

Hancock, J. P. et al. "A rapid and highly selective approach to cell separations using an immunomagnetic colloid" *Journal of Immunological Method* vol. 164, pp. 51–60, 1993.

Liberti, P. A. et al., "Ferrofluid as a matrix or magnetic separations" Proc. 1st John Ugelstad Conf., pp. 47–61, 1991.

Liberti, et al., "Analytical and process–scale cell separation with bioreceptor ferrofluids and high–gradient magnetic separation," in *Cell Separation Science and Technology*, D. S. Kompala et al. eds., American Chemical Society, Washington, D.C., pp. 268–288, 1991.

Kemshead, J. T. "The immunomagnetic manipulation of bone marrow"; in *Bone Marrow Processing and Purging*, A. P. Gee ed., CRC Press, Boca Raton, (1991) pp. 293–305.

Areman, e. M. et al., *Bone Marrow and Stem Cell Processing: A Manual of Current Techniques*, F. A. Davis Company, Philadelphia, pp. 267–285, 1992.

Bieva, C. J. et al., "Malignant leukemic cell separation by iron colloid immunomagnetic adsorption," *Exp. Hematol.* 17:914–920, 1988.

Powers, F. J. et al., "Separation of small–cell lung cancer cells from bone marrow using immunomagnetic beads," in *Bone Marrow Processing and Purging*, A. P. Gee ed., American Chemical Society, pp. 257–267.

Rhodes, E. G. H. et al., "Peanut Agglutinin purging and magnetic microspheres" *Advances in Bone Marrow Purging*, Wiley–Liss, Inc. pp. 139–146, 1992.

Okarma, T. et al., "The ais collector: a new technology for stem cell purification", *Advance in Bone Marrow Purging and Processing, Wiley–Liss, Inc. pp. 487–504, 1992.*

Reading C. L. et al., "Magnetic affinity colloid elimination of specific cell populations from bone marrow". from *Bone Marrow Transplantation: Proceedings of the 3rd International Symposium: Autologous Bone Marrow Transplantation*, Houston, Texas, Dec. 4–5, 1986, pp. 133–142.

Molday R. S. et al., "Immunospecific ferromagnetic iron–dextran reagents for the labeling and magnetic separation of cells." *Journal of Immunological Methods*, 52 1982, pp. 353–367.

Straus, L. C., et al., "Selection of normal hematopoietic stem cells for bone marrow transplantation using immunomagnetic microspheres and cd34 antibody." *American Journal of Pediatric Hematology/Oncology.* 13(2) pp. 217–221, (1991).

Trickett, A. E., et al. "Comparison of magnetic particles for immunomagneti bone marrow purging using an acute lymphoblastic leukaemia model." *Transplantation Proceedings*, vol. 22, No. 5 pp. 2177–2178, (1990).

Padanabhan, R., et al. "Purification of transiently transfected cells by magnetic–affinity cell sorting." *Journal of Immunogentics*, 16 (1989), pp. 91–102.

Gee, A. P., et al. "Pre–clinical studies on bone marrow manipulation." in *Magnetic Separation Techniques Applied to Cellular and Molecular Biology.* Proc. 1st Ugelstad Conf., Apr., 1991 pp. 119–133.

Brun, A. et al., "A new method for isolation of reticulocytes: positive selection of human reticulocytes by immunomagnetic separation" *Blood*, vol. 76, No. 11, Dec., 1990: pp. 2397–2403.

Ganshirt–Ahlert, D. et al., "Detection of Fetqal Tisomies 21 and 18 from maternal blood using triple gradient and magnetic cell sorting" *American Journal of Immunology*, vol. 30, 1993: pp. 194–201.

Damjanov, I. "Biology of disease: Lectin cytochemistry and histochemistry", in *Laboratory Investigation*, The United States and Canadian Academy of Pathology, Inc., vol. 57, No. 1, 1987, p. 5.

Forrest, G. C. et al., "Magnetic particle radioimmunoassay", *Immunoassays for Clinical Chemistry*, Hunter et al., eds., pp. 147–162, 1983.

Muir, P. et al., "Rapid diagnosis of enterovirus infection by magnetic bead extraction and polymerase chain reaction detection of enterovirus rna in clinical specimens." *Journal of Clinical Microbiology*, vol. 31, No. 1, Jan., 1993. pp. 31–38.

Kemshead, J. T. et al, "Magnetic separation techniques: their application to medicine.", *Molecular and Cellular Biochemistry*, vol. 67, pp. 11–18, 1985.

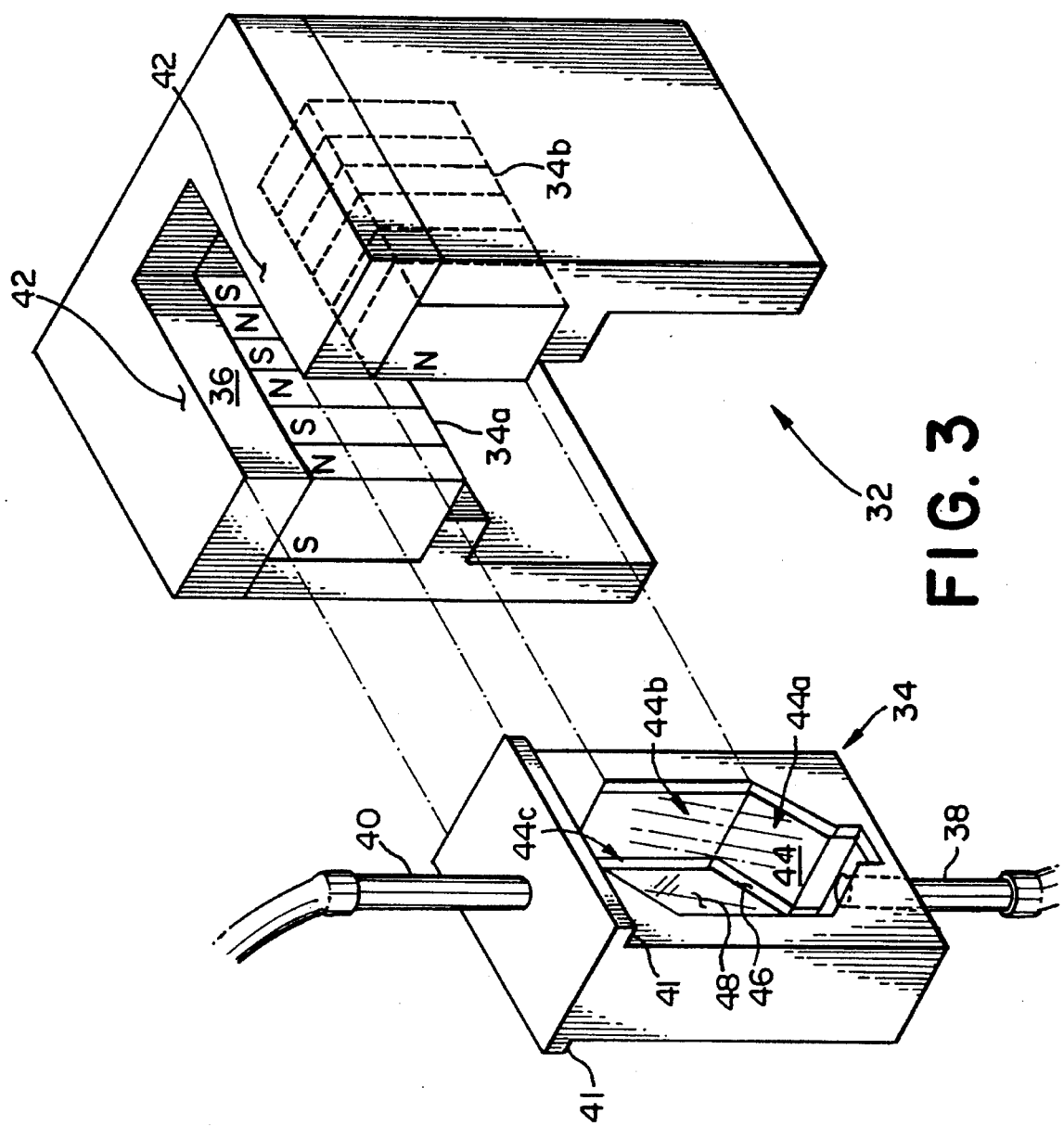

METHOD FOR MAGNETIC SEPARATION FEATURING MAGNETIC PARTICLES IN A MULTI-PHASE SYSTEM

FIELD OF THE INVENTION

The present invention relates to improvements in magnetic separators and methods of separation of magnetic particles and/or magnetic-associated entities from non-magnetic associated entities and media, having particular utility in various diagnostic, therapeutic and industrial procedures involving specific reactions. More particularly, the invention relates to biological separations employing a multiphase liquid system wherein one phase includes a structured magnetic particle phase suitable for transporting other components within the structured phase toward a collection surface of a magnetic separator.

BACKGROUND OF THE INVENTION

Various laboratory and clinical procedures employ biospecific affinity reactions. Such reactions are commonly employed in diagnostic testing of biological samples, or for the separation of a wide range of target substances, especially biological entities such as cells, proteins, nucleic acid sequences, and the like.

Various methods are available for analyzing or separating the above-mentioned target substances based upon complex formation between the substance of interest and another substance to which the target substance specifically binds. Separation of complexes from unbound material may be accomplished gravitationally, e.g. by settling, or, alternatively, by centrifugation of finely divided particles or beads coupled to the target substance. If desired, such particles or beads may be made magnetic to facilitate the bound/free separation step. Magnetic particles are well known in the art, as is their use in immune and other bio-specific affinity reactions. See, for example, U.S. Pat. No. 4,554,088 and Immunoassays for Clinical Chemistry, pp. 147–162, Hunter et al. eds., Churchill Livingston, Edinborough (1983). Generally, any material which facilitates magnetic or gravitational separation may be employed for this purpose.

Small magnetic particles have proved to be quite useful in analyses involving biospecific affinity reactions, as they are conveniently coated with biofunctional polymers, e.g., proteins, provide very high surface areas and give reasonable reaction kinetics. Magnetic particles ranging from 0.7–1.5 microns have been described in the patent literature, including, by way of example, U.S. Pat. Nos. 3,970,518; 4,018,886; 4,230,685; 4,267,234; 4,452,773; 4,554,088; and 4,659,678. Certain of these particles are disclosed to be useful solid supports for immunologic reagents.

Small magnetic particles, such as those mentioned above, generally fall into two broad categories. The first category includes particles that are permanently magnetizable, or ferromagnetic; and the second comprises particles that demonstrate bulk magnetic behavior only when subjected to a magnetic field. The latter are referred to as magnetically responsive particles. Materials displaying magnetically responsive behavior are sometimes described as superparamagnetic. However, materials exhibiting bulk ferromagnetic properties, e.g., magnetic iron oxide, may be characterized as superparamagnetic when provided in crystals of about 30 nm or less in diameter. Larger crystals of ferromagnetic materials, by contrast, retain permanent magnet characteristics after exposure to a magnetic field and tend to aggregate thereafter due to strong particle-particle interaction.

U.S. Pat. No. 4,795,698 to Owen et al. relates to polymer-coated, sub-micron size colloidal superparamagnetic particles. The '698 patent describes the manufacture of such particles by precipitation of a magnetic species in the presence of a biofunctional polymer. The structure of the resulting particles, referred to herein as single-shot particles, has been found to be a micro-agglomerate in which one or more ferromagnetic crystallites having a diameter of 5–10 nm are embedded within a polymer body having a diameter on the order of 50 nm. These particles exhibit true colloidal behavior and do not exhibit an appreciable tendency to separate from aqueous suspensions for observation periods as long as several days.

Another method for producing superparamagnetic colloidal particles is described in U.S. application Ser. No. 07/397,106. In contrast to the particles described in the '698 patent, these latter particles are produced by directly coating a biofunctional polymer onto a pre-formed superparamagnetic crystallite. The resulting particles, referred to herein as DC particles, exhibit a significantly larger magnetic moment than single-shot particles of the same overall size.

Magnetic separation techniques are known wherein a magnetic field is applied to a fluid medium in order to separate ferromagnetic bodies from the fluid medium. In contrast, the tendency of colloidal superparamagnetic particles to remain in suspension, in conjunction with their relatively weak magnetic responsiveness, requires the use of high-gradient magnetic separation (HGMS) techniques in order to separate such particles from a fluid medium in which they are suspended. In HGMS systems, the gradient of the magnetic field, i.e. the spatial derivative, exerts a greater influence upon the behavior of the suspended particles than is exerted by the strength of the field at a given point.

HGMS systems can be divided into two broad categories. One such category includes magnetic separation systems which employ a magnetic circuit that is entirely situated externally to a separation chamber or vessel. Examples of such external separators are described in U.S. Pat. No. 5,186,827. In several of the embodiments described in the '827 patent, the requisite magnetic field gradient is produced by positioning permanent magnets around the periphery of a non-magnetic container such that the like poles of the magnets are in a field-opposing configuration. The extent of the magnetic field gradient within the test medium that may be obtained in such a system is limited by the strength of the magnets and the separation distance between the magnets. As mentioned in Cell Separation: Methods and Selected Applications, Pretlow and Pretlow eds., 1987, p. 262, in reference to external HGMS:

"If one then attempts to scale up the process by increasing the size of the vessel and the magnet similarly, one is often frustrated. The complex geometric aspects of magnetic field generation will not, in general, lead to gradients which still fill the same proportion of the new sample chamber."

Another type of HGMS separator utilizes a ferromagnetic collection structure that is disposed within the test medium in order to intensify an applied magnetic field and to produce a magnetic field gradient within the test medium. In one known type of internal HGMS system, fine steel wool or gauze is packed within a column that is situated adjacent to a magnet. The applied magnetic field is concentrated in the vicinity of the steel wires so that suspended magnetic particles will be attracted toward, and adhered to, the surfaces of the wires. One drawback of such systems is that the use of steel wool or gauze material can entrap non-magnetic components of the test medium by capillary action in the vicinity of intersecting wires or within interstices between intersecting wires. Thus, enlarging the separator serves to increase the amount of non-magnetic components that are so entrapped. Furthermore, an enlarged internal HGMS system, which consequently employs a greater bulk of ferromagnetic material, would suffer from mutual magnetic shielding of the ferromagnetic wire therein.

In both the internal and external HGMS apparatus described above, the limited extent of the high magnetic gradient within the test medium has hampered the ability to process large quantities of material in a conveniently rapid manner. Conventional HGMS separation techniques involve mixing colloidal magnetic particles with a test medium from which a target substance is to be separated. Then, the mixture is introduced into an HGMS apparatus as a single fluid. In order to obtain relatively rapid separations, it has been necessary to use small containers for the test medium in order to generate a sufficiently high gradient extending into the test medium. Increasing the size of the container increases the time required to perform a separation because the superparamagnetic particles most distant from the collection surface are then less responsive to the decreased gradient. Additionally, such particles must travel a greater distance through a relatively viscous fluid in order to be collected.

An internal separator is described in U.S. Pat. No. 5,200,084 employing loops of ferromagnetic wire that are spaced apart from each other. The loops are inserted into a test medium in order to generate an internal field gradient. As in the case of external HGMS systems, increasing the size of the apparatus while maintaining the separation distance between the ferromagnetic collecting wires would have the effect of decreasing the proportion of the volume within the separation chamber in which a high gradient field is present.

High gradient magnetic separation is useful for separating a wide variety of biological materials, including eucaryotic and procaryotic cells, viruses, nucleic acids, proteins and carbohydrates. In methods known heretofore, biological material has been separable by means of HGMS if it possesses at least one characteristic determinant, which is capable of being specifically recognized by and bound to a receptor, such as an antibody, antibody fragment, specific binding protein (e.g., protein A, streptavidin), lectin and the like.

High gradient magnetic separation is a method of choice for separating a cell subset of interest from a mixed population of eucaryotic cells, particularly if the subset of interest comprises but a small fraction of the entire population. Such separation generally relies upon the identification of cell surface antigens that are unique to a specific cell subset of interest. Antibodies directed to these antigens (sometimes referred to herein as "primary antibodies") are utilized directly, by attaching them to magnetic particles, or indirectly, by means of a second receptor/ligand interaction (e.g., avidin-coated magnetic particles recognizing biotinylated primary antibodies, or a second antibody that specifically recognizes an epitope of the primary antibody).

Cell separations are typically performed with one or both of the following objectives: (1) enrichment of a cell type of interest (often a rare cell type) from a mixed cell population; and/or (2) purging of an unwanted cell type (e.g., tumor cells, bacterial contaminants, and the like) from a mixed cell population. Two general approaches have been taken to accomplish one or both of these objectives. In one approach, the target cell types may be isolated by positive selection, wherein the cells of interest are labelled with antibodies and then separated from the remaining unlabelled cells in the population. In another approach, a cell type of interest may be isolated or enriched by "negative depletion," in which one or more unwanted cell types are labelled with antibodies and are then removed from the remaining unbound cell type. Depending on the desired outcome, these approaches have been used singly or in sequential combination.

The choice of positive, negative, or combination separation depends largely upon the subsequent use to which the separated cells will be put, as well as the limitations of currently-available magnetic separation methodologies described above. Positive selection is advantageous because of the relatively high yields and purity of the target cell suspensions obtained, often by means of single-step isolation methods. Positive selection is useful for separating target cells for purposes that do not require that the cells be fully functional, with respect to the availability and competence of cell-surface macromolecules. Such purposes include purging of unwanted cells, isolation of cells for further analysis (e.g., by flow cytometry), or identification of cells for diagnostic purposes. However, if the target cells are intended for re-introduction into a patient (e.g., hematopoietic stem cells from bone marrow or peripheral blood), or for other purposes in which full and unaltered biological functionality is required, it is desirable to obtain the target cells in their fully-functional, or native, condition. Since positively-selected cells are labelled with an antibody or other specific receptor, the target cells may be compromised by alterations or losses of the functionalities associated with the surface antigens to which the antibodies are bound. For example, many surface antigens are receptors that modulate activation of pleuripotent stem cells causing them to differentiate. If it is desired to obtain undifferentiated cells, subjecting the cells to treatment that causes them to differentiate, such as may occur during positive selection, can be counterproductive. As another example, many surface antigens, including the CD34 surface antigen associated with hematopoietic stem cells, are homing molecules that inform the cells where to migrate in the body after the cell has been reintroduced into a patient. Blocking such homing molecules with a binding agent during separation can hinder or prevent this critical specific localization process.

Another concern that arises from the attachment of antibody to cells which are to be re-introduced into a human patient relates to the fact that most monoclonal antibody used in immunological separation are raised in mice. A large proportion of the human population carries antibodies against mouse proteins, due to the common contamination of processed food products with mouse parts. As a result, introduction of mouse protein-bearing cells into a human patient can elicit an immune response which could impair the health and/or recovery of patients who may already be immunologically compromised.

Because of the undesirability of attaching labelling antibodies to certain target cell populations, several methods have been developed to remove these labelling antibodies from the cells. Such methods include (1) incubating isolated target cells with vast excesses of a competitive ligand to shift binding of the antibody from the cell surface to the ligand; (2) chemical methods, such as exposure to low pH or to various chaeotropic agents; and (3) treatment of isolated cells with proteolytic enzymes, Each of the known treatments to remove labelling antibodies from positively selected cells can result in reduced target cell yield due to transfer steps or the rigors of the treatment. More importantly however, these methods have met with limited degrees of success in removal of antibodies from the target cells. Moreover, in the case of the enzymatic treatments, the propensity of the proteolytic enzyme to remove portions of the surface antigen to which the antibody is attached, or to non-specifically cleave other critical antigens on the cell surface, can cause additional undesirable results. For example, in Strauss et al., Am. J. Ped. Hematol. Oncol., 13: 217–221 (1991), chymopapain was found to destroy the epitope of the CD34 surface antigen that recognizes My-10 monoclonal antibodies.

Isolation of target cell types by negative depletion can be desirable because negative depletion avoids some of the undesirable results associated with labelling target cells with antibodies or other receptors. The ability to obtain native cells is important clinically in the isolation of hematopoietic cells, as described above, and may also be desirable in obtaining populations of other target cell types or substances. The major disadvantage of known negative depletion methods is that they typically result in low yield and low purity of the target cell type. This disadvantage is especially pronounced in separations of rare cell types, such as hematopoietic stem cells from bone marrow or peripheral blood, or fetal cells from maternal cell types in maternal blood.

Positive selection and negative depletion have been combined in attempts to increase the yield and purity of target cells. Although some measure of success may be obtained by a combined approach, the disadvantages associated with positive selection remain inherent in a two-step approach. Additional decreased yield and/or functionality can result from the added steps in the separation procedure.

It is apparent that HGMS affords certain advantages in performing separations based on biospecific affinity reactions involving colloidal magnetic particles. Nevertheless, currently available systems are limited with respect to the level of yields and purity achievable. Accordingly, a need exists for HGMS methods and devices that are simple, rapid, and reduce entrapment of non-target substances, thereby achieving both high yield and high purity. It would be of even greater advantage if such results could be obtained by a negative depletion method, wherein the cells or other substances of interest need not be attached to antibody or other receptors in order to be separated from a test medium. Such improvements in magnetic separation technology would clearly be of practical utility in conducting either laboratory- or clinical-scale separations, for diagnostic, therapeutic or preparative purposes.

SUMMARY OF THE INVENTION

This invention provides methods and devices for separating magnetic particles and/or magnetic-associated substances from non-magnetic associated substances and media, which employ a multi-phase liquid system wherein one phase includes a structured magnetic particle phase suitable for transporting other components within the structured phase toward a collection surface of a magnetic separator, thereby to achieve a high level of yield and purity of the separated substance or substances.

According to one aspect of the invention, a method is provided for separating one or more target substances from a test fluid, which comprises mixing the test fluid with a quantity of magnetic particles to produce a suspension, which includes a magnetic component and a non-magnetic component, the target substance or substances being associated with the magnetic component. A magnetically inert fluid phase is established in a container having a collection surface therein, and the aforementioned suspension is introduced into the container as a distinct phase from the magnetically inert phase. The distinct phase is stable within the container, so that the magnetic and non-magnetic components of the suspension are confined within the distinct phase. A magnetic field is generated in the container, and possesses a sufficiently high intensity in a region adjacent the collection surface to cause disintegration of the distinct phase into its constituent magnetic and non-magnetic components. The distinct phase is attracted toward the collection surface, and the magnetic component of the distinct phase is collected upon the collection surface when the distinct phase disintegrates in the region adjacent the collection surface. The non-magnetic component of the disintegrated phase is removed from the region adjacent the collection surface.

The above-described separation method can be used in an externally or internally-generated magnetic gradient apparatus, either in a batch-separation process or in a flow-through process. According to one aspect of the present invention, devices are provided for carrying out the aforementioned methods of the invention to enable convenient and rapid high-quality separations.

It is a further object of this invention to provide separation methods that are simple, rapid and achieve both high yield and high purity of the selected substances. In preferred embodiments, the methods of the invention are used to separate one or more cell subsets of interest from a mixed population of cells. These methods are particularly useful in cases where the cell subset of interest comprises a small fraction of the entire population. These methods ar also useful for removing an unwanted cell type, such as a tumor cell, from a mixed cell population.

From the foregoing background and summary, and the detailed description set forth hereinbelow, it will be appreciated that the present invention provides methods and apparatus which enable the efficient and effective separation of target substance-bearing magnetic particles from non-target substances in a test medium.

BRIEF DESCRIPTION OF THE DRAWINGS

FIG. 3 is a perspective view of an external HGMS apparatus for performing flow through separations in accordance with the invention;

DETAILED DESCRIPTION OF THE INVENTION

I. Multi-Phase Separation

Figure 1A:
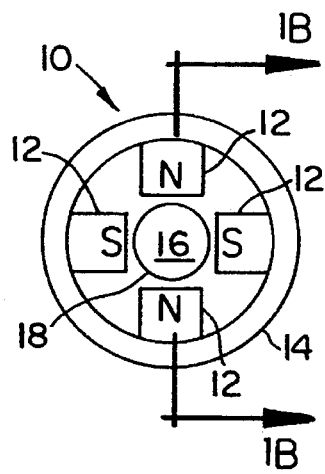
FIG. 1A is a plan diagram of an external HGMS apparatus.

Referring now to FIG. 1A, there is shown an external HGMS apparatus, generally designated as separator 10, that is constructed in accordance with the specification of U.S.

Pat. No. 5,186,827, which is incorporated by reference herein. The separator 10 features a plurality of magnets 12 attached to a yoke 14. The magnets 12 are arranged on the yoke 14 to face a receptacle 16 with alternating magnetic polarity around the periphery of the receptacle 16. The receptacle 16 is adapted to receive a non-magnetic container 18.

The arrangement of magnets 12 around the receptacle 16 generates a magnetic field within the receptacle 16 that is substantially uniform along the peripheral wall of the container 18. In other words, the magnetic field within the receptacle 16 is characterized by contours of equal magnetic flux density that are substantially circular within the receptacle 16, and thus the flux density contours are substantially aligned with the periphery of the container 18. Consequently, the angular component of the magnetic field gradient (i.e. along the peripheral wall of the container 18) is substantially zero, and the magnetic flux density gradient is substantially orthogonal to the peripheral wall of the container 18.

In alternative embodiments, external HGMS separators can be provided having a magnetic field such that similar gradient characteristics are established along a broad portion of a non-magnetic container. Such separators are extensively discussed in commonly-owned U.S. application Ser. No. 08/006,071, now U.S. Pat. No. 5,466,574 issued Nov. 14, 1995 which is incorporated by reference herein.

Figure 1B:
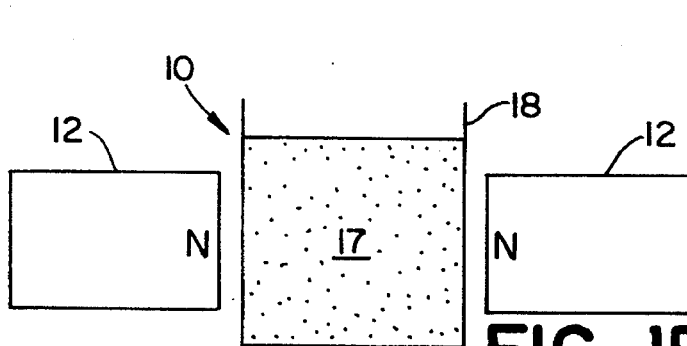
FIG. 1B is an elevational sectional diagram of the external HGMS apparatus of FIG. 1A taken along the line 1B.

In FIG. 1B there is shown a sectional diagram of the external HGMS separator 10. According to a single-phase separation method, a test medium 17 is introduced into the container. The test medium 17 has magnetic particles suspended therein. The magnetic particles preferably have a biofunctional polymer coating that includes a receptor for binding with one or more ligands in the test medium. The test medium is incubated under conditions sufficient to cause the receptor and ligand to bind, and the container is positioned within the separator 10 in order to separate the magnetically-labeled ligand from non-magnetic components of the test medium. The test medium 17 may be introduced into the container 18 prior to positioning the container 18 within the separator 10. Alternatively, the test medium 17 may be introduced into the container 18 after the container has been positioned within the separator 10. In either sequence, it has hitherto been the practice to thoroughly mix the magnetic particles with the test medium, prior to separation, in order to promote binding between receptor and ligand. The test medium is then subject to separation as a single, substantially homogenous liquid phase within the container 17.

Figure 1C:
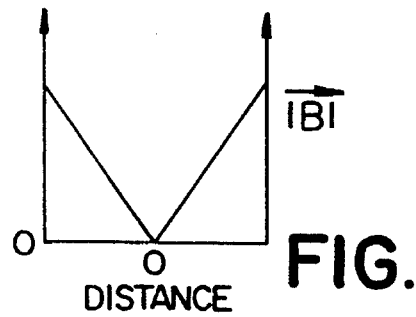
FIG. 1C is a graph of relative magnetic flux density along the line 1A versus distance.

In FIG. 1C, there is shown a graph of the relative magnitude of the magnetic flux density versus distance from the center of the container 18. As can be appreciated, the confronting arrangement of opposing magnetic fields produces a magnetic field that is substantially zero at the center of the container. The magnetic flux density increases, with a roughly constant gradient, with distance from the center of the container, and reaches a maximum value at the peripheral wall of the container. The maximum obtainable value of the magnetic flux density is equal to the flux density at the pole face of either of the magnets 12. The gradient of the flux density is determined by the separation distance between the confronting magnets 12.

A high gradient magnetic field is required in order to effectively transport the magnetic particles toward the peripheral walls of the container. If the container, and the gap between the opposing magnets is enlarged, a longer time is required to separate the magnetically-responsive component of the test medium 17 from the non-magnetic component. Additionally, those magnetic particles which are located in the central portion of the container 18 tend to remain in suspension even after prolonged exposure to the external magnetic field.

In accordance with the present invention, we have discovered that a phase phenomenon (that we believe to be due to mutual interactions between suspended magnetic particles and interactions with the suspension medium) can be exploited to produce and maintain a distinct, structured phase of magnetic particles, or ferrophase, within a multi-phase liquid system. The ferrophase can be used to transport target substances from regions of relatively low magnetic field intensity to regions of relatively high magnetic field intensity within an HGMS apparatus. Such transport of the ferrophase can be accomplished at greater speed than the transport of individual magnetic particles within a single liquid phase as has been hitherto obtained in single phase methods. Additionally, this transport mechanism can be exploited to obtain better control of the collection of the magnetic particles, and other entities associated therewith, upon a collection surface within a separation apparatus.

When a droplet of suspended magnetic particles is introduced into a magnetically inert fluid (i.e., a fluid that is either non-magnetic or weakly magnetic compared to the ferrophase), the magnetic particles within the droplet are subject to influences tending to disperse the particles and are also subject to influences tending to aggregate the particles. An important dispersive influence is thermal diffusion. If the particles have a sufficient magnetic moment, the dispersive influence of diffusion can be balanced by mutual magnetic attraction between particles and, to a lesser extent, by cohesive forces within the liquid component of the ferrofluid. Such balanced interaction between the particles can cause the droplet to form a lattice-like structure, or ferrophase, that remains distinct from the inert fluid. In addition to inhibiting diffusion of the magnetic particles into the inert fluid, the non-magnetic components of the suspension can be inhibited from diffusing out of the ferrophase by interaction between the magnetic particles and such non-magnetic components. Such interaction may be due to viscous effects or to polar electrostatic effects, such as solvation and charge interactions. Hence, a two-phase system, comprising an inert fluid and a ferrophase, can be formed and maintained.

Upon the application of a magnetic field, it is believed that magnetic interaction between the magnetic particles increases. The increased magnetic attraction causes increased stress within the ferrophase, since some particles will experience stronger attraction and other particles will experience stronger repulsion depending upon the positions of the particles within the lattice-like structure. Whether such internal stress is sufficient to destroy the integrity of the ferrophase depends upon the strength of the applied field and the relative importance of fluid viscosity and/or polar electrostatic effects upon the stability of the ferrophase. Under a relatively weak magnetic field gradient, the ferrophase will move relative to the surrounding inert fluid in the direction of increasing magnetic field strength. The non-magnetic components of the ferrofluid will be retained within the ferrophase, and will be transported by the movement of the ferrophase. If the magnetic field intensity continues to increase as the ferrophase moves in the direction of the gradient, the internal stress in the ferrophase will eventually destroy the integrity of the ferrophase and release the non-magnetic component of the ferrophase in the high magnetic field intensity region of the apparatus.

Figure 2A:
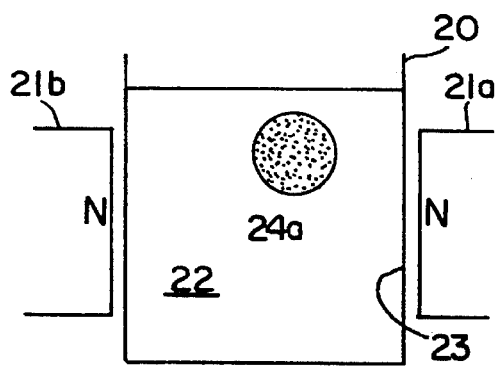
FIGS. 2A–2C are elevational sectional diagrams of an external HGMS apparatus representing successive stages of a separation process in accordance with the invention.

In FIG. 2A, there is shown a non-magnetic container 20 that is positioned between magnets 21a and 21b of an HGMS apparatus. Within the container 20 is an inert fluid 22. The composition of the fluid medium 22 is preferably a buffer solution that is selected to be physiologically compatible with the test medium, or a component thereof, from which a target substance is to be separated. A droplet of magnetic particle suspension, selected to have phase-forming properties, is introduced into the inert fluid 22 and forms ferrophase 24a therein. Such a droplet may be introduced, for example, by pipetting a sample of magnetic particle suspension into the container.

The magnetic particles in the ferrophase may have a receptor thereon for binding specifically with a target substance in the carrier fluid. Alternatively, the magnetic particles may have a common capture agent thereon for binding with one or more receptors of a common class of receptor (e.g., immunoglobulin) that are specifically bound to one or more target substances in the carrier fluid. The various types of binding relationships that may exist within the ferrophase, and their applicability to particular separation techniques are discussed hereinbelow. Generally, the ferrophase 24a comprises a non-magnetic component and a magnetically-responsive component, which includes magnetic particles, and wherein the target substance is bound to the magnetic particles.

With continued reference to FIG. 2A, the relatively weak magnetic field in the vicinity of the ferrophase 24a contributes to the stability of the ferrophase 24a. The field gradient causes the ferrophase 24a to move toward the peripheral wall 23 of the container 20. In addition to being selected on the basis of phase-formation, the magnetic particles are selected to have sufficient viscous and/or polar electrostatic effect to retain the non-magnetic component thereof within the ferrophase 24a as the ferrophase 24a moves toward the wall 23. The movement of the ferrophase 24a is very rapid relative to the movement of individual magnetic particles in a single-phase system as has been discussed in connection with FIG. 1B. One reason for such relatively rapid movement is that the viscous effect between the ferrophase and the inert fluid in the two-phase system is considerably less pronounced than the total viscous effect between all of the magnetic particles and the test medium in the single-phase system.

Figure 2B:
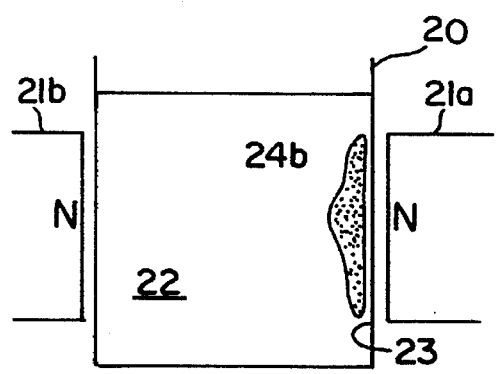
Figure 2C:
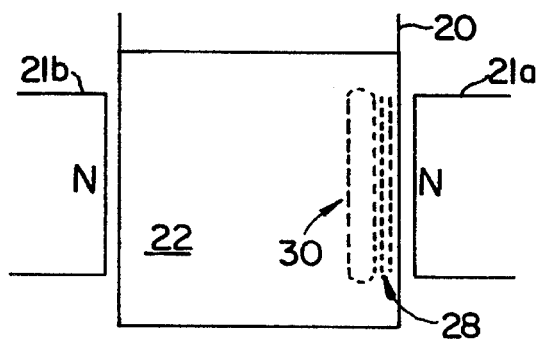

Preferably, the container 20 and the surrounding magnets are arranged such that the magnetic flux density along at least a broad portion of the wall 23 is relatively uniform, while the flux density increases in a direction toward, and the gradient thereof substantially perpendicular to, the wall 23. Hence, as shown in FIG. 2B, the ferrophase will deform to approximate the shape of the uniform field region along the wall 23 as the ferrophase approaches the wall, as indicated by the shape of the deformed ferrophase 24b. As the ferrophase 24b becomes thin and moves close to the wall 23, the high magnetic field intensity in the vicinity of the wall overcomes the stabilizing influences within the ferrophase 24b, hence the magnetic particles are pulled out of the ferrophase 24b. The resulting disintegration of the ferrophase 24b is shown in FIG. 2C wherein the magnetic particles 28 are thinly and uniformly deposited in a layer 28 upon a broad portion of the wall 23. The non-magnetic component of the magnetic particle suspension, at least initially, is released into the magnetically inert phase and will be concentrated in a region of the inert fluid 22 generally designated as enriched region 30.

Since the magnetic particles are preferably collected in a broad thin layer 28 on the wall 23 of the container 20, the quantity of particles within the ferrophase can be controlled to result in a sparse distribution of collected particles upon the wall 23. Such collection over a broad portion of the wall 23 reduces the formation of thick agglomerations, clumps, or spots which would otherwise entrap non-magnetic components of the magnetic particle suspension in interstices between the collected particles. Additionally, since the magnetic particles are initially transported to the high gradient region en masse within the ferrophase prior to the disintegration of the ferrophase, the efficiency of separation between the magnetic and non-magnetic components of the magnetic particle suspension is greatly enhanced relative to single-phase methods.

Yet another advantage of the two-phase method relative to single-phase methods is a relaxation of geometrical constraints that have hitherto limited the useful size of external HGMS separators. For example, use of a multi-phase method eliminates the need to obtain a high intensity field within a relatively large volume of the separation chamber. A high intensity field, sufficient for separating the components of the magnetic particle suspension, is only required in a region immediately adjacent to the collection surface. The remainder of the magnetic field extending within the interior of the separation chamber is only required for attracting the ferrophase toward the collection surface and providing sufficient magnetization of the particles within the ferrophase to maintain the integrity of the phase during transport within the inert fluid.

In alternative embodiments, the order in which the inert fluid and the ferrophase are introduced into the separation container may be reversed from that described above. Similarly, it is not necessary for the separation container to be positioned within the separation apparatus when the ferrophase is established in the inert fluid. We have found that suitable phase-forming magnetic particles will establish a ferrophase, within a magnetically inert fluid, that is resistant to mild agitation, such as may occur when a two-phase system within a non-magnetic container is introduced into the separation apparatus.

In another alternative embodiment, it has been found that the multi-phase separation method is suitable for performing separations on a continuous, or flowthrough, basis. Referring now to FIG. 3, there is shown a flowthrough separation apparatus, generally designated separator 32, and a non-magnetic flowthrough vessel 34. The flowthrough vessel 34 is adapted to be removably inserted into a vertical slot 36 within the separator 32.

The flowthrough vessel 34 includes an inlet port 38 for introducing fluid into a plenum 44. The flowthrough vessel is also provided with an outlet port 40 for conducting a flow of fluid out of the plenum 44. The plenum 44 includes a lower triangular cavity 44a, a central rectangular cavity 44b, and an upper triangular cavity 44c. A pair of flanges having outwardly extending surfaces 41 are attached to the vessel 34, so that the surfaces 41 rest upon upper surfaces 42 of the separator 32. When the vessel 34 is inserted into the separator 32, the vessel 34 is supported within slot 36 by the surfaces 41.

The separator 32 includes two arrays of confronting magnets 34a and 34b. The magnets 34a are mounted adjacent to one another within the separator 32 and facing one side of the slot 36 with alternating polarity. The magnets 34b are mounted upon the separator to face the other side of the slot 36, thus confronting the magnets 34a. The polarity of corresponding pairs of magnets 34a and 34b is the same, so that the arrays of magnets 34a and 34b are in a field-opposing relationship.

During a separation procedure, the vessel 34 is situated within the slot 36 so that the peripheral wall 46 of the rectangular portion 44b of the plenum is adjacent to the array of magnets 34b. The array of magnets 34b generate a magnetic field 44 that is relatively strong within the plenum along a broad portion of the peripheral wall 46 and which is relatively weaker within the interior of the plenum 44 more distant from the peripheral wall 46. Similarly, a peripheral wall 48 on the other side of the plenum 44 from the wall 46 is situated adjacent to the array of magnets 34a. As in the arrangement discussed in connection with FIG. 1A, the field opposing relationship of the magnetic arrays 34a and 34b, and the alternating polarity of magnets within the arrays 34a and 34b provides high magnetic flux density gradients in the directions substantially perpendicular to the opposing peripheral walls 46 and 48. The magnetic field so generated is also characterized by no significant magnetic gradients in directions parallel to broad portions of the walls 46 and 48 in the central portion 44a of the plenum 44.

Figure 4:
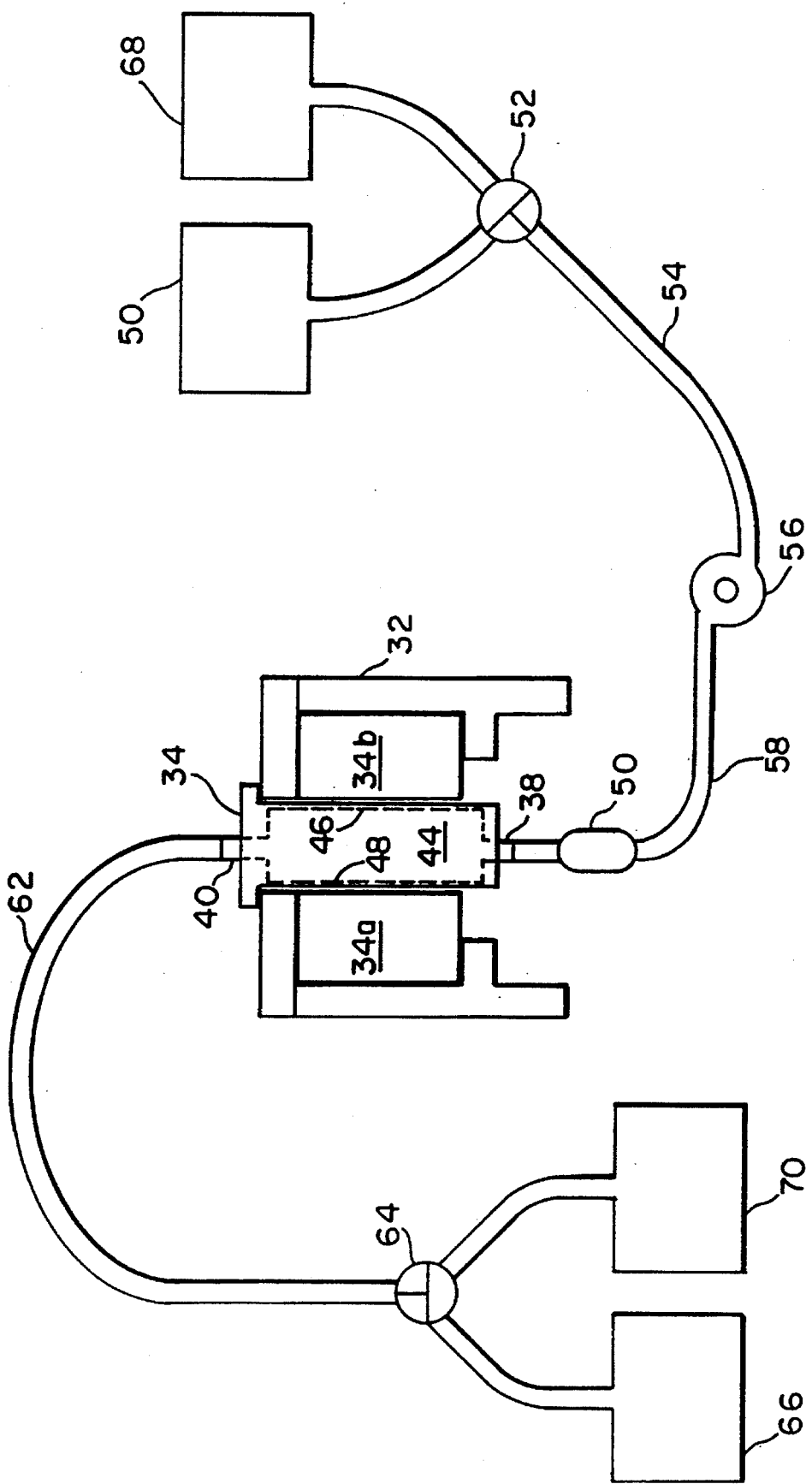
FIG. 4 is a schematic diagram of a system for performing multi-phase separations utilizing the apparatus of FIG. 3.

Referring now to FIG. 4, there is shown an preferred arrangement for performing flowthrough separations in accordance with the dual-phase principles discussed herein. The arrangement of FIG. 4 shall first be described in the context of performing a positive selection separation. In such a procedure, a source of buffer fluid, such as infusion bag 50, is connected to a tee valve 52. The tee valve is initially set to cause the buffer fluid from bag 50 to flow through a conduit 54 to a pump 56. The pump 56 regulates the flow of buffer fluid into a conduit 58. The conduit 58 is connected with the inlet port 38 of the flowthrough vessel 34, which is situated within the separator 32. A bubble trap 60 is preferably connected along conduit 58 for removing bubbles from the fluid stream introduced into the plenum 44 of the flowthrough vessel 34.

In due course, the plenum 44 is filled with the buffer fluid in order to establish the inert phase of the dual-phase system. The flow rate of the buffer fluid in this first part of the procedure, as regulated by the pump 56, may be set to fill the plenum 44 in a conveniently rapid manner. The flow of buffer fluid is continued so that some of the buffer fluid exits the plenum 44 via outlet port 40. One end of a conduit 62 is connected to the outlet port 40 in order to receive the flow of fluid from the outlet port 40. The other end of conduit 62 is connected with a tee valve 64. The tee valve 64 is initially set to receive fluid from the conduit 62 and cause such fluid to be collected into a receptacle 66.

Then, the pump 56 is set to provide a fluid flow that is low enough to prevent strong turbulence in the conduits 54 and 58, and within the plenum 44, that would disrupt the integrity of the ferrophase to be utilized in the separation procedure. The tee valve 52 is then turned to connect the conduit 54 with a source of a phase-forming magnetic suspension, such as an infusion bag 68. The magnetic suspension in the infusion bag 68 may include magnetic particles having a biofunctional coating that have been incubated with a non-magnetic fluid containing cells, cell components, or other target substances having a binding affinity for the biofunctional coating of the magnetic particles.

The magnetic suspension is then conducted along conduit 54, through pump 56 and conduit 58, and into the plenum 44 of the separation vessel 34. Depending upon the flow rate determined by the pump 56, the magnetic suspension may be introduced into the plenum 44 in a continuous stream, or as a sequence of droplets. In either case, the phase forming characteristics of the magnetic suspension cause both the magnetic and non-magnetic components of the suspension to move within the plenum 44 as a distinct phase from the inert phase that was previously established within the plenum 44.

As the ferrophase is transported within the plenum 44, the ferrophase is attracted as a continuous stream toward one of the peripheral walls 46 or 48. Individual droplets of the ferrophase may be individually attracted to either of the walls 46 or 48. As the ferrophase, or portions thereof, approaches the magnetic intensity region in the vicinity of a peripheral wall, the ferrophase is caused to spread out and conform to the substantially parallel contours of equal magnetic flux density along the wall. As the flattened ferrophase continues to approach the peripheral wall, it disintegrates into its constituent non-magnetic and magnetic portions. The magnetic components of the disintegrating ferrophase are rapidly collected upon the peripheral wall of the plenum 44 in a broad, uniform pattern with no significant entrapment of the non-magnetic component. The non-magnetic component of the disintegrating ferrophase is incorporated into the inert phase of buffer solution within the plenum 44.

After the desired quantity of the magnetic suspension from infusion bag 68 has been introduced into the separation vessel, and the magnetic components therein have been collected upon the peripheral walls of the separation vessel, the non-magnetic component of the original magnetic suspension may be further washed out of the separation vessel as follows. The tee valve 52 is again set to conduct a flow of buffer fluid from the infusion bag 50 into the conduit 54. The pump 56 is adjusted to provide a relatively high flow rate of buffer fluid to the inlet port 38 of the separation vessel 34. The flow of buffer fluid is maintained for a sufficient interval to substantially wash the non-magnetic component of the magnetic suspension out of the plenum 44 and into the receptacle 66. During this wash step, the magnetic component of the magnetic suspension remains adhered to the peripheral walls 46 and 48 of the plenum 44.

When the non-magnetic component has been substantially washed from the plenum 44 and from the conduit 62, the flow of buffer fluid into the plenum 44 may be stopped while the separation vessel is removed from the separator 32. Once the separation vessel is removed from the separator, the magnetic component of the magnetic suspension, which had been adhered to the peripheral walls of the plenum, can be resuspended within the fresh buffer. Then, the valve 64 is set to conduct fluid from the conduit 62 into a second collection receptacle 70. A flow of buffer fluid is again conducted from the infusion bag 50 and through the plenum in order to cause the resuspended magnetic component of the suspension to flow into the collection receptacle 70 via the conduit 62. Alternatively, a second buffer fluid, having a significantly higher viscosity and/or density than the first buffer fluid, may be used to effectively sweep the resuspended magnetic component out of the plenum and into the collection receptacle 70. Such a second buffer fluid is preferably discrete from the original buffer fluid, so that the moving boundary between the two buffer fluids urges the resuspended particles into the conduit 62 without significant mixing of the resuspended particles and the second buffer fluid.

In an alternative procedure, the magnetically inert phase of the two-phase separation procedure may be established by conducting an initial single-phase separation of the magnetic suspension. Such an initial separation may be formed by initially filling the plenum with the magnetic suspension at a relatively low flow rate or by filling the plenum and then stopping the flow for a sufficient period of time for single-phase separation to occur. When the single-phase separation has proceeded to the point at which the central volume of the plenum is substantially filled only with the non-magnetic component of the magnetic suspension, then the flow of the magnetic suspension to the plenum may be increased, or restarted, in order to continue the separation in a dual-phase mode. During the dual-phase mode of operation, the flow of magnetic suspension to the plenum may be substantially higher than during the initial single-phase mode since, as has been discussed, it is then no longer necessary to allow for the transport of individual magnetic components from the central portion of the plenum to the collection surface. Such a method of establishing the magnetically inert phase can be employed in both negative depletion and positive selection separations.

The arrangement shown in FIG. 4 can also be used to perform negative depletion separations, wherein it is desired to collect the non-magnetic component of a magnetic suspension. In the performance of such a method, the plenum 44 is initially filled with a magnetically inert fluid, such as a buffer fluid, and any overflow is collected in receptacle 66. Then, a flow of a magnetic suspension is again introduced into the plenum 44 at a flow rate sufficient to prevent strong turbulence from damaging the ferrophase formed within the plenum 44. When the flow of the magnetic suspension is introduced into the plenum 44, the valve 64 is set to collect the fluid emerging from the outlet 40 into collection receptacle 70. As the flow of the magnetic suspension is continuously introduced into the plenum 44, the resulting ferrophase is attracted toward the peripheral walls. The ferrophase disintegrates and releases the non-magnetic component thereof into the buffer solution within the plenum 44. The continued introduction of the magnetic suspension results in continuous release of the non-magnetic component of the suspension into the buffer fluid, hence the fluid stream collected in receptacle 70 includes the non-magnetic component of the magnetic suspension and buffer fluid.

When the desired quantity of the magnetic suspension has been introduced into the plenum 44, the valve 52 is again set to conduct a flow of the buffer fluid from infusion bag 50 into the plenum 44 in order to wash any remaining non-magnetic component of the original magnetic suspension into the collection receptacle 70. Alternatively, a second buffer fluid having a significantly greater viscosity and/or density than the first buffer fluid may be introduced into the plenum 44 in order to sweep the non-magnetic component of the original magnetic suspension out of the plenum 44 while avoiding further dilution of the non-magnetic component by the first buffer fluid. When the non-magnetic component of the original magnetic suspension has been washed out of the plenum 44, through conduit 62, and into the collection receptacle 70, the valve 64 is closed and the collection receptacle 70 can be removed.

Figure 5:
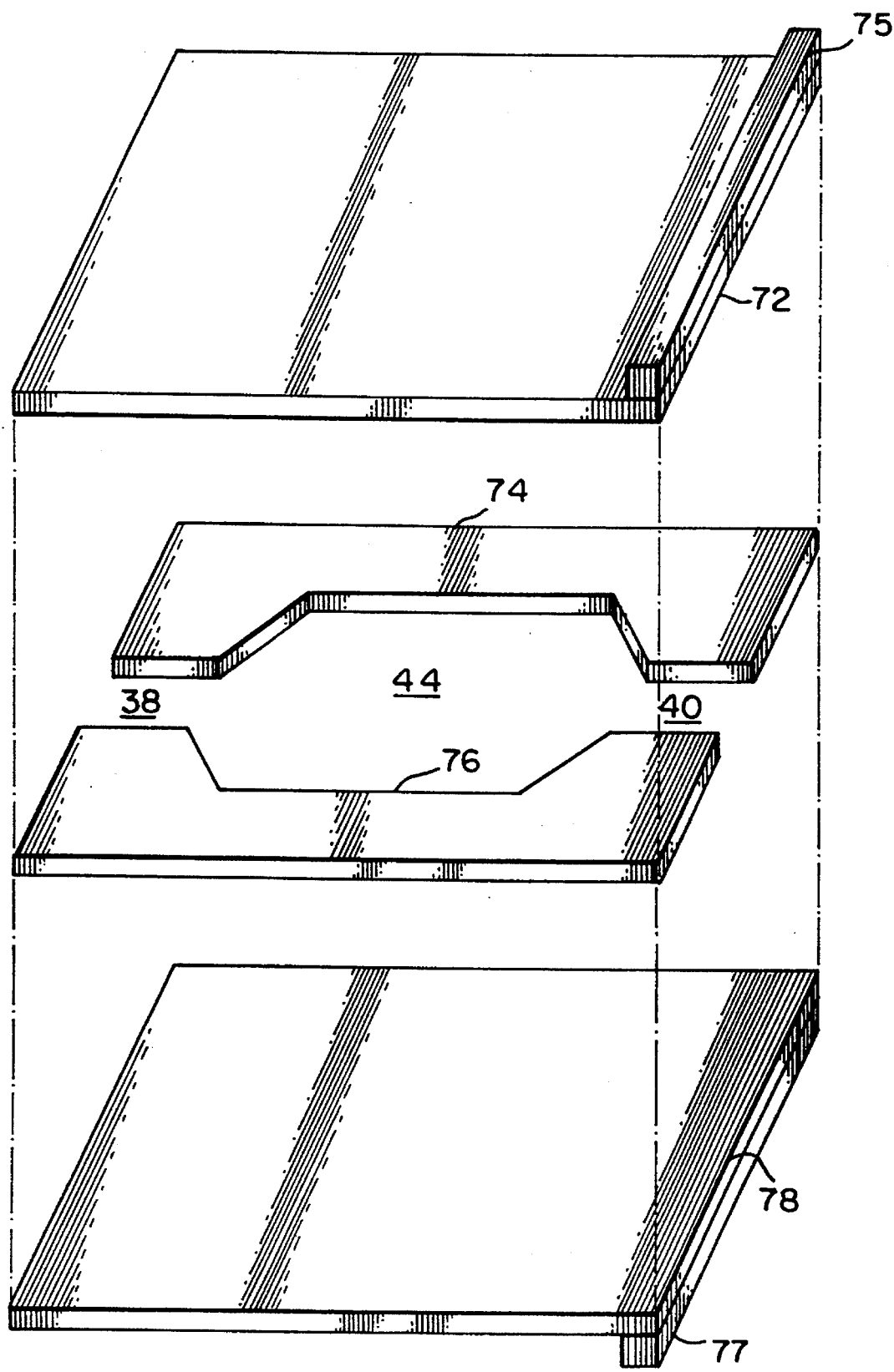
FIG. 5 is an exploded perspective view of the separation vessel utilized within the apparatus of FIG. 3.

In a preferred embodiment, the separation vessel is constructed as shown in FIG. 5. Two sheets 72 and 78, of a material such as LUCITE, form the peripheral walls of the separation vessel. The sheets 72 and 78 are aligned with and bonded to respective upper and lower surfaces of plenum side pieces 74 and 76. The plenum side pieces 74 and 76 are shaped as shown in order to form inlet port 38, plenum 44, and outlet port 40, when they are bonded to the sheets 72 and 78. Additionally, rectangular pieces 75 and 77 are bonded to the outer surfaces of the sheets 72 and 78 in order to form the outwardly extending surfaces for holding the separation vessel within the separator.

The advantages that may be obtained by continuous multi-phase separation relative to continuous single phase separation are similar in nature to the advantages obtained in batch multi-phase separation, i.e. greater speed, enhanced separation efficiency, and relaxation of geometric constraints upon the design of the separation apparatus. An additional advantage provided by the continuous multi-phase process is that by maintaining laminar flow in the plenum and by collecting non-magnetic component of the ferrophase via the auxiliary outlet, significantly less dilution of the non-magnetic component occurs in the flowthrough process than in the batch process. Thus, the continuous multi-phase process is particularly suitable for collection of native populations, or subpopulations, of rare non-magnetic components of the magnetic particle suspension.

Although the dual-phase separation principles are described in detail herein in connection with external HGMS systems, it is recognized that the advantages provided hereby are also applicable to dual-phase separations that can be performed within internal HGMS systems. Of course, internal dual-phase separations rely upon a ferrophase to transport magnetic and non-magnetic components of a magnetic suspension toward a ferromagnetic collection structure having a collection surface disposed within a non-magnetic container. Such apparatus are described in U.S. Pat. No. 5,200,084, which is incorporated by reference herein.

It is noted that in the performance of such multi-phase separations, it is necessary to select a magnetic suspension that will have the requisite phase-forming property relative to the magnetically inert phase of the liquid system. It is additionally desirable for the magnetic suspension to possess a viscous effect and/or polar electrostatic effect sufficient to contain the non-magnetic component of the suspension within the ferrophase during transport toward the collection surface. As mentioned above, the formation of a suitable ferrophase depends upon obtaining a balance between cohesive and dispersive interactions within the magnetic suspension and relative to the magnetically inert phase of the system in which a multi-phase separation is to be performed. Several parameters which affect the influence exerted by such cohesive and dispersive interactions are: the size and mass of the magnetic particles employed, the magnetic moment of the particles, the viscosity of the non-magnetic component of the magnetic suspension, and van der Waals forces or other electrostatic interactions within the suspension. Several environmental parameters; such as temperature, turbulence, the strength of the magnetic field, and the magnetic field gradient in the separation chamber; will also affect the stability of the ferrophase and the efficiency with which components thereof may be separated.

In aqueous solutions, we have found that magnetic particles having an effective core size on the order of tens of nanometers, such as from about 50 nm to 200 nm are capable of forming stable ferrophases at room temperature and at concentrations corresponding to an Iron-equivalent from about 0.01 mg/ml and above. At the lower concentrations, turbulence becomes an important determinant of the stability of the ferrophase. At larger particle sizes, the magnetic interaction between the particles becomes strong enough that the dispersive influences, such as thermal diffusion, are not sufficient to prevent the particles from agglomerating. In solutions of greater viscosity, larger particles and/or lower concentrations of particles may be satisfactorily employed to form and maintain stable ferrophases.

Electrostatic interactions among the particles, and between the particles and the non-magnetic fluid component of the magnetic suspension can, in aqueous solutions of biological components, be reduced by adding casein, polymethacrylic acid, or other materials in order to passivate chemical coordination sites of the surface of the particles. However, the degree of influence upon ferrophase stability that may be exerted by the use of polar solvents or other fluids having a significant propensity toward van der Waals interactions, should be empirically determined in advance of performing a multi-phase separation.

The concentration of particles is most conveniently expressed in terms of iron-equivalent concentration since, in separations employing receptor-ligand binding, more than one particle may bind to a particular ligand. For example, a cell membrane may possess numerous sites to which a receptor-coated magnetic particle may attach. The term "iron-equivalent" is used herein to denote the mass of iron corresponding to the magnetic relaxivity of the actual material used to form the core of the magnetic particles. Example 1 hereinbelow demonstrates ferrophase separation conducted using unbound magnetic particles. Other examples hereinbelow demonstrate ferrophase separation conducted using bound magnetic particles bound to various target substances.

Figure 6:
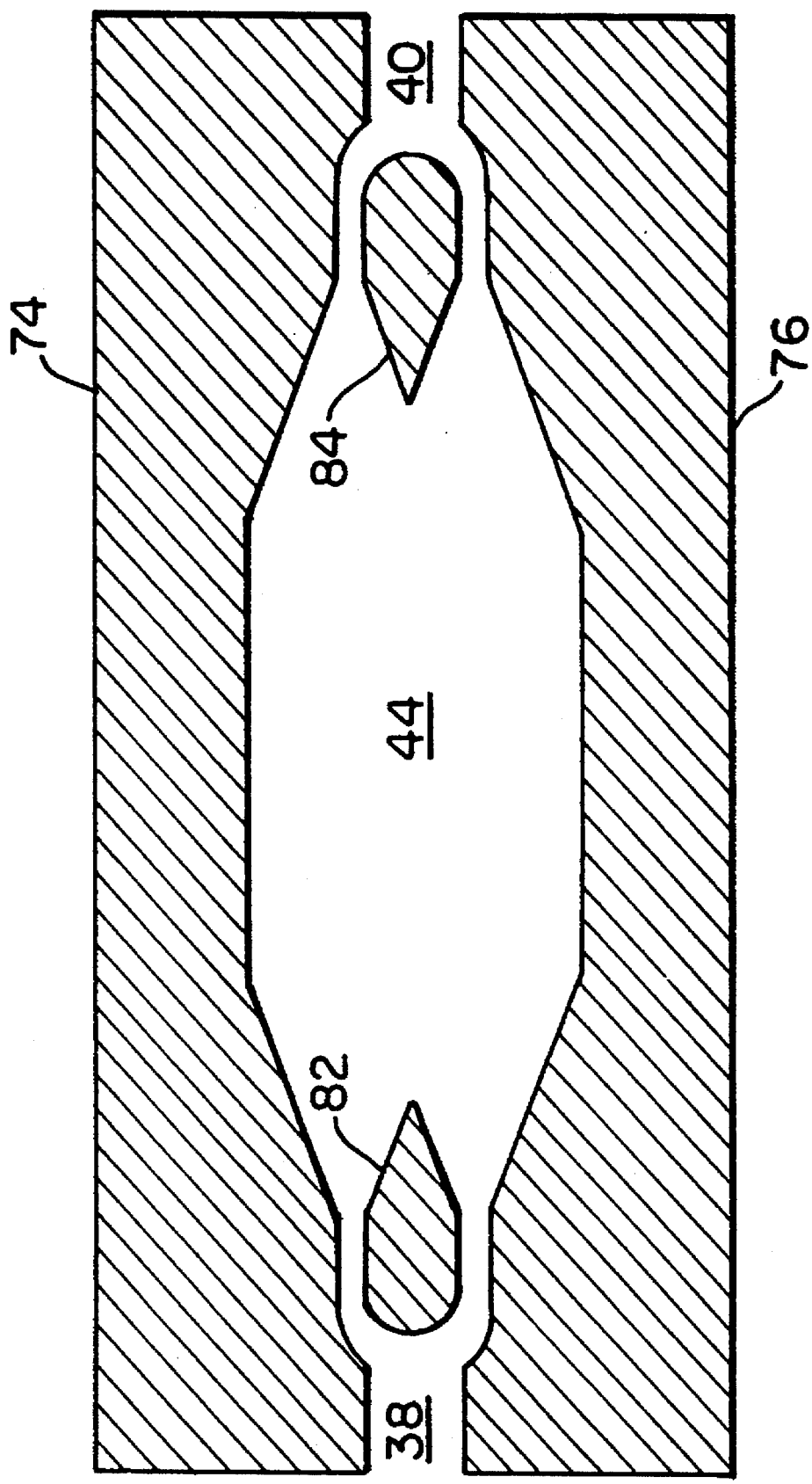
FIG. 6 is a sectional view of an alternative separation vessel having reduced turbulence.

At the lower concentrations, turbulence becomes an important determinant of the stability of the ferrophase. Using the separation apparatus shown in FIG. 4, we have found that aqueous concentrations of magnetic particles on the order of less than 0.010 mg Fe/ml should be introduced at a flow rate of below 1 ml/min. At higher concentrations, such as above 0.010 mg Fe/ml, the magnetic suspension can be introduced into the plenum at up to 10 ml/min. The dimensions of the rectangular portion of the plenum are preferably 1.2 inches wide, 2.8 inches long, and 0.25 inches deep. As can be appreciated, it is desirable to supply fluid to the separation vessel via standard laboratory tubing. Thus, the cross-sectional width of the fluid flow must, at some point, be increased from the width of the tubing to the width of the broad collection surface of the plenum. Such an increase in width occurs in the triangular portion of the plenum that is adjacent to the fluid inlet port. At low magnetic particle concentrations, and/or at high flow rates, the Venturi effect in the triangular portion of the separation vessel may cause undesirable eddy currents or turbulence that could damage the integrity of the ferrophase. A preferred manner in which such turbulence may be reduced is shown in FIG. 6. In addition to the plenum side pieces 74 and 76, a hydrodynamic damping structure, such as a spoiler 82, is positioned adjacent to the inlet port 38 in order to promote laminar flow within the plenum 44. A similar spoiler 84 is positioned adjacent to the outlet port 40. The separation vessel of FIG. 6, referred to hereinafter as a "dual channel" separation vessel, provides the ability to form stable ferrophases at reduced particle concentrations and/or higher flow rates relative to the separation vessel 34 of FIG. 3. Other hydrodynamic damping structures may be effectively utilized within a flow through separation vessel to achieve similar results. For example, in an alternative embodiment, a plurality of cylindrical obstructions, or baffles, are vertically positioned at the locations occupied by spoilers 82 and 84 in FIG. 6.

The range of magnetic field gradients that have been successfully used to attract the ferrophase to the vicinity of the peripheral wall of the separation vessel range from about 3 Kgauss/cm to about 20 Kgauss/cm. These gradients were obtained by using rare earth permanent magnets, such as Nd-Fe-B magnets, providing a measured field of about 4 Kgauss at the pole faces thereof. The gradient in the separation chamber can be adjusted by selecting an appropriate gap spacing between opposing magnets on either side of the chamber.

In the absence of significant electrostatic interaction within the ferrophase, the influence of viscous effect between the magnetic particles and the non-magnetic component of the ferrophase is an important determinant of the ability of the ferrophase to remain integrated as it is transported toward the collection surface of a separation chamber. In general, it is desirable to utilize a magnetic suspension wherein the Reynolds number of the magnetic particles remains below unity until the ferrophase disintegrates in the high gradient region. The effective Reynolds number of a magnetizable particle increases in the presence of a magnetic field, hence the Reynolds number of the non-magnetized suspension should be several orders of magnitude lower than unity, such as below about $10^{-5}$, prior to introduction into a separation apparatus. Of course, this condition may be considerably relaxed in the presence of significant attractive electrostatic effects within the ferrophase. Such electrostatic effects are particularly pronounced for very small particles, on the order of tens of nanometers in diameter, which have a high surface to volume ratio compared to larger particles (1 μm and above).

It is contemplated that applications may arise wherein it is desirable to use an available non-phase forming magnetic particle system in order to carry out a particular separation. Such an instance could arise, for example, wherein economy dictates the use of a commercially available receptor-coated particle over the use of a custom lot of prepared phase-forming particles. In order to take advantage of the multi-phase method of separation, it is possible to supplement the non-phase forming particles with a sufficient concentration of phase forming particles, which would not necessarily participate in receptor-ligand binding but would enable ferrophase formation for the purpose of transporting the non-phase forming suspension toward the collection surface of a high gradient separator.

II. Magnetic Separation of Cells and Other Biological Substances

The multi-phase magnetic particle system described herein can be used to improve many separation applications in which HGMS is currently utilized. Referring to biological substances that can be separated, these include eucaryotic and procaryotic cells, subcellular organelles, viruses, proteins, nucleic acids, carbohydrates, ligands or complex molecules comprising nucleic acids, proteins, lipids and/or carbohydrates. A biological material is separable by the methods described herein if the material possesses at least one characteristic determinant, which is capable of being recognized by and bound to a receptor. Biological materials having such characteristic determinants are referred to herein as "target substances." If the target substance is a cell, it is referred to herein as a "target cell." The term "characteristic determinant" is used herein to refer to substances such as antigens, haptens, and other complex molecules (e.g., carbohydrates, glycoproteins, etc.), which are capable of the above-described specific binding to a receptor. "Receptor" is used herein to refer to any substances or group of substances having a specific binding affinity for a given characteristic determinant, to the substantial exclusion of other substances. Monoclonal antibodies are preferred for use as the receptor. However, polyclonal antibodies or non-antibody receptors, including antigens for antibody-producing cells or antigen processing cells, lectins, such as concanavalin A and various agglutinins, biotin-labelled reagents or hapten-labelled reagents, may be used, if desired.

The methods of the invention may be structured as "direct" or "indirect" protocols, or some combination thereof. In the direct protocol, the receptor is attached directly to the magnetic particles, and a magnetic suspension is obtained by incubating test samples containing the target substance with the receptor-coated particles. In the indirect protocol, the target substance is incubated with a free receptor and the magnetic particles comprise a capture agent capable of recognizing and binding specifically to the receptor, so as to form a complex comprising target substance, receptor, capture agent and magnetic particle.

For the indirect protocol, suitable capture agents include Protein A or Protein G, where immunoglobulin is used as the receptor; avidin, where a biotin-labelled reagent is used as the receptor; and anti-hapten, where a hapten-labelled reagent is used as the receptor. Either biotin or a hapten may be used to facilitate capture of lectin receptors, e.g., concanavalin A and various agglutinins, which bind selectively to membrane-containing target substances whose characteristic determinants comprise carbohydrate or glycoprotein components. Hapten/anti-hapten pairs suitable for this purpose include dinitrophenol (DNP)/anti-DNP, fluorescein/anti-fluorescein or arsanilic acid/anti-arsanilic acid.

The magnetic separation methods and devices of the invention may be used to carry out cell separation for isolation and/or analysis of specific cell populations. Because high levels of recovery and purity are achievable by the methods of the invention, these methods are particularly suitable for removal or isolation of rare cells from a mixed population of cells. Such separations include, but are not limited to, enrichment of stem cells from bone marrow or peripheral blood, isolation of fetal cells from maternal blood, isolation of transfected cells, and removal or isolation of tumor cells from various mixed cell populations. Such separations may be accomplished by positive selection or negative depletion, or both, in accordance with the present invention. (It will be appreciated that, according to the definition of "target cell" set forth above, a cell subset enriched by negative depletion is actually a non-target cell, since it is not bound to an antibody or other receptor. Instead, cells to be depleted from the population are target cells, within the definition.) Cells recovered by such separation methods may be utilized for numerous purposes, including further analysis (e.g., by flow cytometry or other methods) or for therapeutic purposes (e.g., re-introduction of enriched populations of stem cells to patients).

Although the use of the methods and devices of the invention are exemplified herein by the separation of rare cell populations, as described above, it will be apparent to those of skill in the art that the methods may also be used for other separations according to the same general procedures. These include, but are not limited to, the separation of various bacteria and parasites from fecal matter, urine, sludges, slurries and water (e.g., ground water or streams); or in the separation of various bacteria, fungi or other target substances from food products or other sources.

The preferred magnetic particles for use in carrying out this invention are particles of a size and composition such that they exhibit phase-forming behavior relative to a selected magnetically inert fluid, as described hereinabove.

Magnetic particles having the aforementioned properties can be prepared as described in U.S. Pat. No. 4,795,698, the entire disclosure of which is incorporated by reference in the present specification, as if set forth herein in full. Methods for using these magnetic particles are described in application Ser. No. 08/006,071, now U.S. Pat. No. 5,466,574 issued Nov. 14, 1995 also incorporated herein by reference in its entirety. These particles, referred to as "single-shot" particles, possess sufficient magnetic moment to be of use in certain embodiments in the present invention, including static separations and dynamic separations under appropriate conditions.

It is preferred for practice of the present invention to use magnetic particles prepared as described in co-pending application Ser. No. 07/397,106, also incorporated by reference in its entirety. With respect to cell separations using antibodies as the receptor, it was further discovered that use of the DC ferrofluids enabled the labelling antibody concentration to be as low as, e.g., 0.1 µg (or less, depending on binding affinity) per ml of cells, while still achieving highly effective separation.

Ferrofluids comprising magnetic particles to which the receptor has been directly attached may be used for practice of the present invention. Such ferrofluids are sometimes referred to herein as "direct receptor ferrofluids." However, it is preferable to use ferrofluids comprising magnetic particles to which are attached a capture agent capable of binding specifically to a class of receptors, such as a secondary antibody directed to the Fc portion of a primary antibody, or streptavidin for the capture of biotinylated receptors. Ferrofluids comprising such capture agents are sometimes referred to herein as "common-capture ferrofluids."

In cell separations employing either the direct or indirect protocols described above, the mixed cell population comprising target cells is preferably disposed in a physiologically buffered solution. Such buffers are well known in the art and comprise, for example, phosphate-buffered saline (PBS) containing 0.5% bovine serum albumin (BSA) and, optionally, 0.2% sodium azide ($NaN_3$). The buffer should be isotonic, with a pH of about 7. Ferrofluids may be prepared in a similar buffer, but comprising casein instead of BSA.

If desired, receptor- or capture agent-coated ferrofluids may be magnetically enriched by the addition of uncoated magnetite particles, such that the final concentration of iron in the ferrofluid preferably ranges between 10 and 100 µg/ml. Such magnetic enrichment may be employed to enhance the phase-forming characteristics of the resulting suspension. Magnetic washing buffers are also utilized in some embodiments of the invention. These may be prepared by suspending an aliquot of weakly magnetic ferrofluid, such that it will not be separated in the field gradient on a time scale comparable to that required for ferrophase transport.

In the preferred embodiment of cell separation wherein the characteristic determinant is a cell surface antigen and the receptor is a surface antigen-specific antibody, it is desirable to adjust the antibody concentration to achieve optimally effective separations. In positive selection procedures, it is common to use only one specific antibody directed to the target cells. In contrast, negative depletion methods often employ several different specific antibodies, each directed to a cell subset to be depleted from the sample, thereby enriching the sample a selected cell population. One significant advantage of the methods of the invention is that very low concentrations of such antibodies may be utilized, for reasons set forth hereinbelow.

In the typical immunospecific indirect method of separating the target cells, it is customary to incubate cells with a cell-specific monoclonal antibody (MAb), wash out excess MAb and then incubate with a multivalent common capture agent (e.g., secondary antibody or avidin) on a suitable solid support, such as magnetic particles. The purpose of removing excess MAb is to prevent agglutination between non-cell bound MAb and the multivalent common capture agent, and also to preserve binding sites on the common capture agent. With the use of solid supports of microscopic nature, such as magnetic particles, there is an additional basis for the need to first wash out excess MAb, which results from the tendency for common capture colloids to agglomerate with free MAb in solution. Since many magnetic beads are close in size to cells (e.g., 1–5 μm) a potential exists for forming agglomerates in which non-target cells can become entrapped.

In experiments employing the common capture ferrofluids described above, we found that those ferrofluids could be added to the separation mixture without first removing excess MAb without resulting in entrapment of cells in the ferrofluid matrix. Surprisingly, allowing the excess MAb to remain in the separation mixture was found to enhance separation. By way of explanation, we believe that the common-capture ferrofluids do indeed agglomerate with free MAb in solution, but these agglomerates remain small because the total antibody concentration in the solution is low. Such small agglomerates do not contribute significantly to entrapment of the non-target cells, which are much larger than the agglomerates. Instead, these small agglomerates bind to MAbs attached to cells, or form magnetically-attached networks of multivalent antibodies accumulating from MAbs bound to cells, causing significantly greater quantities of magnetic material to be "loaded" onto a target cell. Thus, the overall magnetism of the target cell is increased. Such multivalent networking phenomena are commonly observed and exploited in immunological separation techniques. However, the phenomenon is not restricted to immunoglobulins; any multivalent common capture agent should exhibit the same behavior. Indeed, the same behavior has been observed in systems utilizing biotinylated antibodies as receptors, and streptavidin as the common capture agent.

Conditions that contribute to the optimization of the aforementioned multivalent networking phenomenon include: (1) a ferrofluid concentration such that there is sufficient capacity for the ferrofluid to interact with MAbs in solution, and with MAbs bound on target cells (antibody may be added in excess to accomplish this); (2) a common capture agent that is sufficiently polyvalent to bind several MAbs; and (3) relative MAb and ferrofluid concentrations such that agglomerates of these reagents free in solution will form slowly, while those agglomerates developing from targeted cells will form more rapidly. Given that targeted cells do indeed serve as concentrated regions for MAbs, this latter condition is easily achieved.

The added magnetic load imparted to target cells by way of the polyvalent networking phenomenon described above (sometimes referred to herein as "chaining") is advantageous in several respects. These include: (1) cells having greater magnetic loads are more easily separated from the ferrophase and collected upon a surface at lower magnetic gradients; (2) simplified processing of cells and enhanced viability thereof by omitting the step of washing free monoclonal; and (3) the excess MAb in solution drives the equilibrium reaction between the MAb and the cell surface antigen toward the bound state, which is advantageous, particularly with low affinity antibodies.

As mentioned above, the chaining phenomenon may be adapted for use with biotinylated MAbs as the receptor and streptavidin as the common capture agent in the ferrofluid. In this case, the specific binding site of the monoclonal antibody attaches to the cell surface antigen, and the polyvalent networking phenomenon occurs by way of streptavidin binding to biotin. To optimize this system, the monoclonal antibody should be multiply labelled with biotin; 4–8 biotins per MAb molecule is optimal. Similarly, to optimize the chaining reaction in systems employing a secondary antibody as the common capture agent, we have determined that a polyvalent goat antibody reacting with approximately six determinants on the primary MAb yields optimal results. It is important to note that the chaining phenomenon can be made to promote removal of excess MAb from solution, which is desirable if the target cells are desired to be free of MAb attachment. MAb removal via the chaining phenomenon may be performed through the use of streptavidin or avidin as the common capture agent.

Because target cells are integral participants in the above-described chaining process, it has been discovered that, when targeting mixtures of distinct populations of cells, it is possible to use lowered concentrations of each targeting antibody. For example, if an optimal concentration of labelling antibody for targeting one population is 0.5 μg/ml, then in using three antibodies against three distinct populations, each MAb concentration may be dropped to approximately 0.15 μg/ml. The likely reason for this is that chaining is independent of antibody specificity, therefore, any of the three monoclonals introduced into the system will participate in a chaining reaction occurring in relation to a particular targeted cell. Additionally, a chaining phenomenon contributes substantially to separation of cells, as described above, while lowering the concentration of a specific antibody results in a concomitant decrease in the number of cell surface determinants labelled. This is advantageous because it enables separation of cells over a wide concentration range, using the same optimum concentration of antibodies.

Because of the numerous advantages associated with the polyvalent chaining phenomenon described above, it is preferable to optimize the separation reaction to facilitate the occurrence of this phenomenon. However, it should be appreciated that effective separations may be achieved even in the absence of chaining, by employing the multi-phase system described herein.

In an alternative method, chaining can be caused to occur by using a first ferrofluid having a specific receptor for the target cell. Then, a second ferrofluid may be added which has a receptor specific for the first ferrofluid.

In addition to the advantages described hereinabove, the indirect separation protocol offers the additional advantage that, once an optimal concentration of labelling monoclonal antibodies has been determined for a given cell population, the concentration of cells which can be isolated at that optimum antibody concentration may vary over a wide range. The theoretical basis for this feature is illustrated in Table 1, which shows the relationship between target cell concentration in a mixture of cells and the concentration of free monoclonal antibody after equilibrium is reached, within a given set of parameters. In the example illustrated in Table 1, it is noteworthy that over three orders of magnitude change in target cell population results in a degree of saturation of cell determinants that is virtually equivalent. Moreover, it can be seen that most of the labelling antibody remains free in solution, such that the concentration of antibody available for participation in the polyvalent chaining phenomenon is approximately the same regardless of the number of target cells in the mixture. When the antibody concentration is increased (2–5-fold over the concentrations shown in Table 1), the saturation values have been found to increase to 80–90%. Under those conditions, the range of free monoclonal antibodies becomes even smaller for the corresponding cell concentration range shown.

TABLE 1

Relationships Between Target Cell Concentration and Unbound MAb Concentration

| % Target cell in mixture | $M_{CD}$* | % Saturation | Free MAb % |
|---|---|---|---|
| 30% | $2.5 \times 10^{-10}$ | 62.4 | 84.3 |
| 3% | $2.5 \times 10^{-11}$ | 66.3 | 98.3 |
| 0.3% | $2.5 \times 10^{-12}$ | 66.6 | 99.8 |
| 0.03% | $2.5 \times 10^{-13}$ | 66.7 | 99.9 |

*Molarity of characteristic determinants (CD)

Thus, the number and concentration of monoclonal antibodies may be adjusted to accommodate either a positive selection strategy or a negative depletion strategy. The total antibody concentration is preferably less than about 1.5 μg/ml, but can be as high as about 5.0 μg/ml, and the preferable range of concentration of each determinant-specific antibody should be between about 0.05–0.2 μg/ml. For a positive selection strategy for separating one target cell population, for example, the cell determinant-specific MAb may be provided at 0.15 μg/ml, and the total antibody concentration may be increased to, e.g., 0.6 μg/ml by the addition of non-specific antibody. It will be appreciated that the non-specific antibody should be similarly labelled, or obtained from the same species of animal as the specific antibody, to facilitate the polyvalent chaining phenomenon as described above. For negative depletion strategies wherein several populations of cells are desired to be removed from a mixed cell population, several specific MAbs may be mixed together (e.g., 12–15 MAbs) with each MAb being present at a concentration of, e.g., 0.1–0.15 μg/ml, the total concentration of antibody thus not exceeding the preferred maximum concentration of about 1.5 μg/ml. Again, it will be appreciated that all monoclonal antibodies utilized in a multiple depletion strategy should be similarly labelled, or should be obtained from the same animal species.

For cell separations, the mixed population of cells is typically obtained from various body fluids, such as bone marrow, blood, urine, sputum or secretion, using standard procedures for obtaining the desired mixed cell population from these biological sources. For the direct labelling protocol, ferrofluids comprising specific antibodies as receptors are added to the test medium in buffered solution as described above. For the indirect labelling protocol, free receptor (e.g., MAb) is added to the mixed cell population, and pre-incubated prior to the addition of common-capture ferrofluids. Incubations of cells and MAbs are typically conducted at room temperature or at a temperature slightly above the freezing point of the cell suspension (i.e., 4° C.). The period of incubation is normally or relatively short duration (i.e., about 2–30 minutes). The cell suspension may be agitated or stirred during the incubation period to facilitate contact between the receptor and the cell surface determinant. In the indirect protocol, common capture ferrofluid is thereafter added to the MAb-labelled cell suspension, and incubated as described above.

Ferrofluid/cell suspensions typically comprise between 5 μg/ml and 100 μg/ml of ferrofluid, and preferably between 10 μg/ml and 50 μg/ml. In any event, the concentration of ferrofluid should not exceed 1 mg/ml, nor be less than 0.1 μg/ml. These concentrations of antibody and ferrofluid in the cell suspension contribute to the ability of ferrofluid to form a ferrophase when placed in the magnetic field of the separation chamber.

In a preferred embodiment, MAb and ferrofluid concentrations may be manipulated so as to maximize cell labelling and polyvalent chaining and minimize amounts of free MAb and ferrofluid required for the separation process. For example, cells may be incubated with MAb at a MAb and cell concentration significantly higher than that used for separation. Increasing cell and MAb concentration shifts the equilibrium of the system to favor the binding reaction. The system is then diluted, thereby dropping cell and MAb concentration. If this step is performed quickly, no significant dissociation of MAbs from cells takes place.

After binding of the receptor to the target substance is allowed to occur, magnetic separation of the magnetic particles from the suspension is performed using the methods and devices of the present invention. The suspension is placed in or passed through a suitable separation vessel for batch-wise or continuous processing in a manner which establishes a distinct phase relative to a magnetically inert fluid phase in the vessel, as described hereinabove.

In accordance with the present invention, it has been discovered that the ability of certain magnetic suspensions to form distinct phases in fluid media can be exploited to facilitate better separation by establishing a ferrophase in a separation chamber before the test sample containing magnetically labelled target cells is introduced or, as in the preferred embodiment, by forming the phase first by either a static separation of ferrofluid and/or ferrofluid-labeled materials prior to initiation of flow.

In a preferred embodiment of the invention, the techniques described hereinabove for (1) optimizing ferrofluid and antibody concentration, (2) facilitating the polyvalent chaining phenomenon in an indirect labelling methodology and (3) pre-establishing ferrophases in the magnetic separation chamber, may be utilized to accomplish massive negative depletion to recover rare cell populations (e.g., stem cells, fetal cells) with a level of purity and yield that heretofore has not been easily or reasonably achievable by other methods. In fact, this massive negative depletion can match or exceed separation efficiencies achievable in positive selection methods, with the added advantage that the cells of interest need not be labelled with antibody. By way of example, the methods of the invention are capable of effecting recovery of a 5% population of cells by depletion of cells comprising the remaining 95% of the population, with a yield of 80–90% of that 5% population at a level of purity greater than 90%. A 1% population of cells can also be isolated at similar yields by way of negative depletion of the remaining cells in the population. A model system for negative depletion of human peripheral blood mononuclear cells is described in detail in Example 5.

In another preferred embodiment, the methods and devices of the invention are applied to a protocol for the purpose of isolating cell populations of interest and/or purging a mixed cell population of a particular unwanted cell type, such as a tumor cell. Such methods are described in detail in Examples 2, 3, 4, 5 and 6. Using such methods, a mixed cell population containing 10% of the target cells to be removed was depleted of 99% of the target cell after magnetic separation. In another experiment, depletion of over 99.9% of target cells from a starting sample containing up to 10% of those cells was obtained.

The methods and devices of the present invention may be used to particular advantage in a combined strategy for isolating a small population of rare cells (e.g., stem cells, fetal cells) from a mixed cell population, while simultaneously purging the population of unwanted cells (e.g., tumor cells). This may be accomplished simply by incorporating a receptor for the unwanted cell type in the negative depletion separation systems described hereinabove. It will be appreciated that, in cases wherein the unwanted population comprises a subpopulation of cells already targeted for depletion in such a system, no additional antibodies need be added. One example of this situation is in various leukemias, wherein the unwanted target cell populations are B-cells, already targeted for removal in the hematopoietic stem cell enrichment process. In other embodiments, additional monoclonal antibodies directed to various tumor cells or other unwanted cells are added to the negative depletion antibody mix.

The reagents and compositions described hereinabove for practicing methods of the present invention may be conveniently assembled as kits. For example, a fetal cell separation kit may include: (1) ferrofluid such as a common-capture ferrofluid (e.g., goat anti-mouse ferrofluid) or direct-labeled ferrofluid (e.g., anti-CD71); (2) a panel of monoclonal antibodies for targeting and depleting maternal cells (e.g., leukocytes, maternal lymphocytes, non-nucleated erythrocytes); and (3) detailed directions for use of the kit, including preparation of various dilution buffers, if such buffers are not provided with the kit. Such a kit may further include a disposable cell separation chamber, as well as reagents for further analysis of the isolated fetal cells of interest (e.g., probes for detecting genetic abnormalities, such as those associated with chromosomes 21, 18, 13, etc., and numeric anomalies of X and Y chromosomes) or reagents (such as fetal stem cell factor for the expansion of fetal stem cells from maternal circulation, either for diagnostic or therapeutic purposes). Alternatively, a kit could contain reagent for DNA analysis or detection using such methods as PCR.

Similarly, a kit for enriching hematopoietic stem cells may comprise a common-capture ferrofluid and a panel of monoclonal antibodies directed to lineage-determined cells in a mixed cell population, such as peripheral blood or bone marrow. Likewise, purging kits may be assembled which include monoclonal antibodies directed to a specific cell type desired to be removed from a mixed cell population. Other combinations and kits may be assembled, which will be apparent to one skilled in the art.

The following examples further describe in some detail the manner and process of using the devices and methods of the present invention and set forth several preferred embodiments for practicing the invention. These examples are intended to illustrate, rather than to limit the invention.

EXAMPLE 1

Dual Phase and Single Phase Separations with Phase-Forming and Non-Phase-Forming Particles A. Dual-Phase Separation In order to demonstrate the phase-forming property of DC colloidal particles, the following experiment was performed. A colloidal suspension of covalently coupled streptavidin-direct coated ferrofluid (Immunicon Corp., Huntingdon Valley, Pa., lot #STA 0294-1193-OD2) was prepared using an imidazole buffer and having an Iron-equivalent concentration 0.413 mg/ml. The DC suspension was diluted 1:1 with blue food coloring, resulting in an Iron-equivalent concentration of 0.207 mg/ml. The core size diameter of these particles was approximately 50 nm. Including the polymer coating, the total size of these particles was approximately 120 nm. Hence, the concentration of particles in this suspension was approximately $8.25 \times 10^{11}$ ml$^{-1}$.

A 50 µl sample of the suspension was pipetted into a microtiter well located in a quadrupole separation apparatus and containing 200 µl of water.

Upon introduction to the microtiter well, the ferrofluid suspension immediately migrated within the well to form a substantially uniform layer distributed around the peripheral circumference of the microtiter well. The appearance of the water in the central portion of the well remained clear and colorless, indicating that the blue dye was transported toward the wall without significantly dis-associating from the ferrofluid. Thus it was established that the technique of separately introducing ferrofluid into an inert medium is capable of transporting a non-magnetic component therein toward a collection surface without significant mixing of the non-magnetic component with the inert medium.

B. Comparative Single-Phase Separation

In order to demonstrate the result obtained in an equivalent single phase process, the microtiter well was then removed from the quadrupole separator, and the liquid therein was vigorously mixed by pipet agitation in order to form a single liquid phase within the well. After mixing, the well was again placed in the separator. Initially, the fluid in the well was dark brown in color—corresponding the presence of the suspended colloidal particles. During the course of one minute following placement of the container within the separator, the liquid therein became progressively lighter in color. At the end of one minute, the magnetic particles were again adhered to the wall as before, and the liquid in the well was pale green. The pale green color of the liquid in the well was similar to the color obtained in a control well containing an equivalent dilution of the food coloring in water.

Thus, the non-magnetic component of the ferrofluid was dispersed throughout the container, rather than being separated from the ferrofluid in an enriched region near the peripheral wall. Additionally, the separation process required substantially more time than the immediate result obtained in the two-phase procedure.

C. Formation of Enriched Region

In order to establish separation of the non-magnetic component of the ferrofluid in an enriched region, a two phase separation was again carried out in accordance with Part A above. Then, the liquid within the well was agitated while the well remained in the separator. Agitation of the liquid within the well resulted in a pale green color throughout the well, similar to that obtained with the equivalent dilution of the food coloring.

D. Effects of Particle Concentration and Turbulence

In order to determine the effect of magnetic particle concentration upon the tendency to form a ferrophase, a second dilution of ferrofluid and blue food coloring was prepared. In this second dilution, the Iron-equivalent concentration was 0.020 mg/ml. This concentration, corresponding to a particle density of approximately $7.98 \times 10^7$ ml$^{-1}$, is similar to that used in many cell separations.

50 µl of this ferrofluid was then pipetted into to a microtiter well positioned within a quadrupole separator and containing 200 µl of water. The magnetic particles were immediately observed to collect uniformly upon the peripheral wall of the well. In this experiment, the blue food coloring did not migrate to the wall of the well and the water within the entire well was observed to be colored.

A second trial was performed using this lower concentration of ferrofluid. During this second trial, the ferrofluid was pipetted more slowly into the microtiter well, taking care to avoid strong turbulence at the point of introduction into the well. The result of the second trial was that the ferrofluid migrated toward the wall in a visible stream from the pipet tip and was collected upon the peripheral wall of the container. The water remained colorless as in the first trial using the higher concentration of ferrofluid.

E. Non-Phase-Forming Particles

A sample of commercially available magnetic beads (DYNABEADS, HLA Cell Prep II, Dynal product #219.03) was obtained and diluted with blue food coloring to a concentration of $4 \times 10^8$ ml$^{-1}$. These beads were characterized by a diameter of 4.5 μm and a saturation magnetization of $56.7 \times 10^3$ A/m.

50 μl of the dilute beads was pipetted into a microtiter well positioned within a quadrupole separator and containing 200 μl of water. When the beads were introduced into the water, they immediately migrated to the well wall, leaving a localized region of colored water at the point of introduction. The same results were obtained in additional experiments which were conducted using bead concentrations of $2 \times 10^7$, $2 \times 10^6$, and $2 \times 10^5$ ml$^{-1}$.

The normal range of concentration at which these beads are employed to perform biological separations ranges from about $10^5$ to about $10^6$ ml$^{-1}$. As was found in Example 1-D, an increased concentration of submicron colloidal particles tended toward an increased phase-forming ability. However, with particles having an increased size and decreased magnetic moment, such as DYNABEADS, no indication of phase-forming ability was found at concentrations more than ten times the normal operating concentration.

EXAMPLE 2

Mixed Tissue Culture Cell Lines as a Model System for Tumor Cell Purging

Preparation of cells: CEM cells (ATCC Accession No. CCL 119) and Raji cells (ATCC Accession No. CCL 86) were centrifuged at 400 g for 10 min. The Raji cell pellet was resuspended in 1 ml of IPBS buffer (PBS, containing 0.5% BSA, 0.2% NaN$_3$) and to which 100 ul Hoechst A 33342 (1 ug/ml conc.) super vital dye was added. After 30 min. incubation at 37° C. cells were washed 2× with IPBS and resuspended in 10 ml of IPBS at $1.9 \times 10^6$ cell/ml. To 20 ml of CEM cells at $5.1 \times 10^6$ cell/ml ($102 \times 10^6$ total CEM cells) 5.3 ml of Raji cells at $1.9 \times 10^6$ cells/ml were added ($10.07 \times 10^6$ Raji cells total). The total cell mixture was then adjusted to 30 ml with IPBS. The final cell mixture was $112.07 \times 10^6$ total cells at an approx. 1:10 ratio Raji (B cells)/CEM(T cells).

Antibody Preparation: Antibody incubation was carried out at room temperature by adding 300 ul each of CD19 and CD20 (AMAC Inc., Westbrooke, Me.) at 100 ug/ml MAb concentration to the 30 ml starting cell solution and incubated for 30 minutes at room temperature. Cell and antibody mixture was then brought up to 91 ml with IPBS.

Ferrofluid Preparation: Covalently coupled goat anti-mouse Fc-direct coated ferrofluid (Immunicon Corp., Huntingdon Valley, Pa., lot # GAMC E0393-1051-MX, approx. 161 nm in diameter) was magnetically enriched and recovered in 1% casein in PBS and 0.2% NaN$_3$. Two ml of ferrofluid ([Fe]=0.574 mg/ml) was pre-incubated for 20 min. with 8 ml of a 1% casein-PBS buffer. Ten ml of ferrofluid was then added to 91 ml of cells and MAb mixture, incubated at RT for 30 min. and 1 ml of this mixture removed and set aside before magnetic separation. Final separation conditions in 100 ml: $1.12 \times 10^6$ cells/ml, 0.6 ug/ml MAb (0.3 ug/ml of each MAb CD19 and CD20), and 11.4 ug Fe/ml ferrofluid.

Magnetic Flowthrough Separation—

Preparation of magnetic wash buffer: 2.5 ml of weakly magnetic ferrofluid at [Fe]=0.4 mg/ml was incubated with 10 ml of a 1% casein/PBS buffer for 20 minutes at room temperature. Just prior to use the mixture was adjusted to 100 ml with IPBS buffer.

Separation Chamber: Flow cell chamber (polycarbonate) with 3 cm×7 cm×0.5 cm separation space (11.5 ml fluid volume) and two baffles of circular type at the inlet was used for the separation. The flow direction was against gravity at a flow rate of 4.75 ml/min using a peristaltic pump (LKB Microperpex, rate setting 44) fitted with Tygon tubing. The collection line was parallel to the flow direction.

Magnetic Separation: The separation chamber was primed with approx. 30 ml of wash buffer and then 100 ml of cell mixture was run through the system. Volume fractions of 10 ml each were collected for analysis. The chamber was then washed with 50 ml of was buffer, drained and the bound cells in the chamber collected outside the magnetic field using 10 ml IPBS buffer which had been added to the chamber, shaken and the resultant cells and ferrofluid collected.

Analysis of Cells: A 25 ul analysis sample from each fraction was collected in duplicate. In addition, a 25 ul 10× sample was collected (10 ml fraction pelleted at 800×g for 10 min. and resuspended in 1 ml of IPBS), also in duplicate. Samples were placed on dot pre-cleaned, pre-printed slides (Carlson Scientific Inc., Peotone, Ill.), air-dried and the number of Raji cells (blue nuclear stained) viewed and counted using UV microscope (Olympus model TO41), excitation filter pack, 350 nm, with UV emission at 490 nm.

Results: Collection pattern of cells (Raji) were uniform and formed a monolayer as determined on the cell collection chamber by both light and UV microscopic analysis. Negative depletion efficiency of Raji cells at a 10% spike level was 99% in the recovered cells vs. starting cells.

EXAMPLE 3

Peripheral Blood Purging Model Tumor Cells (Raji) Spiked into Peripheral Blood Mononuclear Cells (PBM's)

Cell Preparation: Raji cells (ATCC Accession No. CCL86) approx. 30 ml at $1.0 \times 10^6$ cells/ml were centrifuged at 400 g for 10 min. and the cell pellet resuspended in 1 ml of IPBS. Cells were then labeled with 100 ul Hoechst A 33342. After labeling at 37° C. and washing, the pellet was resuspended in 7 ml of IPBS at $5.4 \times 10^6$ cells/ml. Human peripheral blood buffy coat (approx. 60 ml) was obtained from the American Red Cross (Phila., Pa.). Forty ML of buffy coat was mixed with 60 ml of IPBS buffer and the mixture was carefully layered onto lymphocyte (ficoll) separation media (Polysciences Inc., Warrington, Pa., cat #21463) in 50 ml centrifuge tubes and centrifuged at 800 g for 25 minutes.

The peripheral blood mononuclear enriched interface (PBM) was carefully removed and washed 2× with IPBS. After the last wash the cell pellet was adjusted to $1.75 \times 10^7$ cells/ml in a 15 ml volume for a total cell number of $262.5 \times 10^6$ cells/ml. To 15 ml of PBM cells 4.8 ml Raji cells were added, to give a final cell mixture of $25.9 \times 10^6$ Raji in $262.5 \times 10^6$ PBM, or approx. 9% spike of stained Raji B cells. Flow cytometry analysis (EPICS XL Coulter Corp., Hialeah, Fla.) with FITC labeled CD22 (B cells) demonstrated 4% level in PBM pre-spiked and 14% level of positively after addition of Raji cells into the PBM' fraction.

Antibody Preparation: Antibody incubation was carried out at 4° C. on ice using biotinylated CD19 (Cal tag) and CD20 (Coulter Corp.) by adding 3 ug/ml of each MoAb to 20 ml of the cell mixture.

Ferrofluid Preparation: Stock streptavidin direct coat ferrofluid (Immunicon Corp., lot #0793-1131-OD2, approx. size 135 nm) (magnetically enriched) was used for common capture of targeted B cells. Two ml of ferrofluid at 0.5 mg Fe/ml was pre-incubated with 8 ml of 1% casein-PBS blocking buffer with 0.2% $NaN_3$ one hour prior to use. 6.6 ml of pre-blocked ferrofluid was added to the cell mixture, incubated for 30 min. on ice, and brought up to 30 ml with IPBS just prior to magnetic separation.

Magnetic Flow Through Separation: A dual channel flow cell chamber with 2.8×1.137 in.×0.215 in. separation space (11.2 ml separation volume) was used. Flow direction was against gravity using a LKB microperpex peristaltic pump (rate setting 30) at a flow rate of 3 ml/min. The chamber was primed with 30 ml PBS, 5% BSA, 0.2% $NaN_3$ drained and the separation sample introduced. Five ml fractions of the flow through was collected. Immediately after the cell separation, 50 ml of a wash buffer (PBS with 5% BSA) was introduced at the same flow rate in order to eliminate tailing of cells. The chamber was then drained and 15 ml of IBPS buffer added to the chamber. The chamber was then removed from the magnetic field, manually shaken and the magnetically separated cells recovered.

Analysis of Cells: Duplicate 25 ul samples from each fraction were collected and placed on 10 dot pre-cleaned, pre-printed slides for UV analysis of Raji cell depletion. Each fraction was counted on a hemocytomer for total cell counts, as well as concentrated spotted onto 25 ul 10 dot slides, dried and then observed for Hoechst labeled cells. Flow cytometry analysis was carried out using FITC label MAb CD22 on a Coulter EPICS XL.

Results: Flow cytometry analysis of 10,000 cells in the lymphoid cell-gate revealed 14% of the starting PBM/Raji cell spike was CD22 positive, while cells in the flow through fractions revealed <0.2% CD22 positivity, which was the same as the negative control. This represented removal of B cells to below the level of detection by standard flow cytometry methods. Hoechst labeled Raji cells in the flow through demonstrated greater than three log (99.9%) removal when compared to starting cell populations.

EXAMPLE 4

Mixed Tissue Culture Cell Lines as a Model for Rare Cell Enrichment Via Negative Depletion Preparation of cells: Pre-washed (IPBS) CEM cells were labeled with ethidium bromide (stock 10 mg/ml in $H_2O$) at 5 ul per ml of cells for 45 minutes at 37° C. and washed 3× in IPBS. The cell mixture contained 99% Raji cells, and approx. 1% CEM cells as determined by hemocytometer in a 10 ml volume with a total cell number of 135×10$^6$. Cell counts were performed using a manual hemocytometer and/or Coulter Counter model ZF (Coulter Corp., Hialeah, Fla.). Cell number was confirmed by flow cytometry analysis (EPICS XL Coulter Corp.)

Antibody Incubation: To the 10 ml cell mixture 1.62 ug/ml (0.8 ug/ml of each MAb of biotinylated MAb CD 19/CD20 was added and incubated for 20 minutes at room temperature. Streptavidin ferrofluid (see Example 3) was then added to the cell and monoclonal antibody mixture, incubated at room temperature for 10 minutes and the final volume adjusted to 27 ml with IPBS. The final separation conditions were volume=27 ml, [MAb]= 0.6 ug/ml, streptavidin ferrofluid [Fe]=15 ug/ml, and cell concentration=5× $10^6$ cells/ml.

Magnetic flow through separation: Magnetic flow through separation was performed as described in Example 3 using the dual channel flow cell chamber with slight modifications. The flow rate was 5 ml/min. and nine fractions collected each containing 3 ml.

Cell analysis: Each fraction collected was spotted onto 10 spot slides (25 ul) dried and then observed for ethidium bromide stained cells. Total cell counts were done by hemocytometer. Flow cytometer analysis of ethidium bromide stained cells were performed on each fraction that had been first concentrated (centrifuged) then fixed with 500 ul of 1% paraformaldehyde PBS.

Results: Based on flow cytometry analysis of a starting CEM cell population of approx. 1% flow through fractions collected gave an average purity of 95% (ranges of 85.1–98.1%) with a Raji cell depletion of greater than or equal to three logs (99.9%).

EXAMPLE 5

A Model System for the Negative Depletion of Human Peripheral Blood Mononuclear Cells as a Method for Enriching Rare Cells Cell preparation: Target cells to be enriched were mouse T thymoma cell line EL4 (ATCC Accession No. TIB39). Cells were pelleted at 400×g for 10 minutes, resuspended in IPBS and labeled with ethidium bromide, as stated in Example 4. This cell line had been previously tested for reactivity with biotinylated anti-human MAb CD38 and CD45 by flow cytometry (Coulter EPIC XL) using indirect FITC conjugated streptavidin and found to be non-reactive.

Peripheral blood mononuclear cell preparation was obtained by ficoll density gradient centrifugation of a leukocyte buffy coat unit obtained from the American Red Cross as described in Example 3.

Antibody Incubation: Biotinylated MAb against human CD38 (Caltag) and CD45 (Sigma) was added to 10 ml of PBM with a 1% EL4 spike. Cell counts were done by hemocytometer and confirmed by flow cytometry. To the total cell concentration of 1×$10^8$ cells per 10 ml (1×$10^7$ per ml) 0.3 ug/ml of each biotinylated MAb was added (0.6 ug/ml, or a total of 6 ug MAb). Cells and MAb were incubated for 25 minutes at room temperature. Streptavidin ferrofluid (see Example 3) was added to the cell and monoclonal antibody mixture and incubated for 10 minutes at room temperature then adjusted to the final separation volume of 40 ml with IPBS. The final separation conditions were volume =40 ml, MAb=0.6 ug/ml, streptavidin ferrofluid [Fe]=20 ug/ml, and cell concentration=2.5×$10^6$ cells/ml.

Magnetic flowthrough separation: Magnetic flowthrough separation was performed as described in Example 3 using the dual channel flow cell chamber with slight modifications. The flow rate was 5 ml/min and eight 5 ml fractions were collected.

Analysis of Cells: Cell counts were performed by hemocytometer and cell enrichment and distribution analyzed by flow cytometry as stated in Example 4. In addition, each fraction collected was spotted onto 10 spot slides (25 ul) air dried and then observed for ethidium bromide stained cells. Cell smears were made on chemically clean glass slides, air dried, fixed in methanol and stained with Leukostat (Fisher Scientific) for differential cell analysis.

Results: Based on flow cytometry analysis of the starting EL4 cell population of approx. 1% enrichments of >90% purity were obtained with PBM cell depletions >99.9% and yields of starting EL4 cells recovered >75%.

EXAMPLE 6

Depletion of Neuroblastoma Cells from a Mixed Leukocyte Population

Preparation of Cells: Neuroblastoma cells (IMR32, ATCC Accession No. CCL127), approximately 30 ml at $1.0 \times 10^6$ cells/ml were centrifuged at 400 g for 10 minutes and the cell pellet resuspended in 1 ml of IPBS. Cells were then labelled with 100 µl Hoechst A 33342 as described in Example 2. After labelling at 37° C. and washing, the pellet was resuspended in 7 ml of IPBS at $5.4 \times 10^6$ cells/ml. Human peripheral blood leukocytes (approximately $270 \times 10^6$ cells) was obtained in a "leukocyte" pack from the American Red Cross (Philadelphia, Pa.). Leukocytes were subjected to ficoll density gradient centrifugation as described in Example 3, then resuspended in IPBS at a concentration of $10^7$ cells/ml. IMR cells and peripheral blood leukocytes were combined and adjusted to a final volume of 10 ml with IPBS, to a final total cell concentration of $30 \times 10^6$ cells/ml ($27 \times 10^6$ peripheral blood leukocytes, $3 \times 10^6$ IMR32 cells/ml).

Antibody preparation: Antibody incubation was carried out at 4° C. on ice using a biotinylated α-neuroblastoma antibody panel (10 µg) comprising 13A, thy1, 5.1.H11 in 10 ml of the cell mixture.

Ferrofluid preparation: Stock streptavidin DC ferrofluid magnetically enriched, (see Example 3) was used for common capture of IMR32 cells. 2 ml of ferrofluid at 0.5 mg Fe/ml was pre-incubated with 18 ml of 0.5% casein/PBS blocking buffer with 0.2% $NaN_3$ 1 hour prior to use. The pre-blocked ferrofluid was added to the cell mixture, incubated for 30 minutes on ice, and adjusted to 30 ml with IPBS just prior to magnetic separation.

Magnetic Flow Through Separation: Magnetic flow through separation was performed as described in Example 3 using the dual channel flow cell chamber with slight modifications. The flow rate was 5 ml/min and 12 fractions were collected, each containing 3 ml.

Cell analysis: Cell counts were performed by hemocytometer and cell enrichment and distribution analyzed by flow cytometry as described in Example 4. In addition, each fraction collected was concentrated and spotted onto slides with 5 µl wells, dried, and then observed for Hoechst labelled IMR32 cells.

Results: Based on a total cell count from all fractions of $212 \times 10^6$ cell, the separation yielded a flowthrough fraction with a IMR32 cell depletion of approximately 99.97% ($0.01638 \times 10^6$ IMR32 cells present in the flowthrough fraction, as compared to $212 \times 10^6$ total cells from fraction).

EXAMPLE 7

Use of Ferrophases to Control Movement of Components Disposed Therein

Since ferrophasing can control the movement of a bolus or stream of ferrofluid by subjecting them to appropriate magnetic gradients, there is another application which is not related to separations. To understand this, consider a large opened topped vessel filled with solvent (aqueous or nonaqueous). If a magnet is placed at the side of the vessel at some distance from the top of the liquid and ferrofluid introduced in a bolus or as a stream, providing the ferrofluid is influenced by even the smallest amount of gradient, the ferrofluid will move directly to the region of highest gradient, i.e., directly onto the spot adjacent to the magnet. If the ferrofluid is composed of magnetic particles which are too weak to separate in the gradient applied, the phase will stay in place for long periods of time and behave as if it were contained within a membrane chamber. Further, if the magnet is moved about the side of the vessel, the ferrophase will follow the magnetic gradient.

In one experiment, a bolus of ferrofluid was introduced into a flowing tube (75 mm×200 mm) and held in position at the side of the tube in a 25 mm "patch" by holding a magnet of 25 mm length directly against the side of the tube. Next, the bolus was moved through the tube against flow and could be positioned at will. The ability to move ferrophases in this fashion has significant potential for moving reagents within a reactor using external manipulation. This clearly has industrial uses as well as medical applications. Currently, catheters are used to place materials in various parts of the body for a variety of applications (diagnostic, therapeutic). By appropriate use of gradients, the same could be accomplished with ferrophasing. Further, with ferrophasing, material can be held in place and prevented from being swept away.

While various aspects of the present invention have been described and exemplified above in terms of certain preferred embodiments, various other embodiments may be apparent to those skilled in the art. For example, the method of the invention is suitable for scale-up to accommodate large volumes of material for various industrial processing applications, especially involving biological materials. Accordingly, the invention is not limited to the embodiments specifically described and exemplified, but is capable of variation and modification, within the scope of the appended claims.

What is claimed is:

1. A method of separating at least one target substance from at least one non-target substance in a test fluid, comprising the steps of:

mixing the test fluid with a quantity of magnetic particles to produce a suspension comprising a magnetic component and a non-magnetic component, wherein the magnetic component comprises magnetic particles bound to said target substance through at least one substance on the surface of the magnetic particles which directly or indirectly binds to said target substance and the non-magnetic component comprises the remainder of the test fluid, including said non-target substance, and wherein the magnetic particles possess properties necessary for the formation of a phase which contains both the magnetic and non-magnetic components and which is distinct from a magnetically inert fluid phase of a liquid system in which the separation of target substance occurs;

establishing the magnetically inert fluid phase in a container having a collection surface therein;

introducing said suspension into the container as a stable phase which is distinct from the magnetically inert phase, to confine the magnetic and non-magnetic components of the suspension within the distinct phase;

generating in the container, a gradient magnetic field having a region of sufficiently high intensity adjacent to the collection surface to cause disintegration of the distinct phase into its constituent magnetic and non-magnetic components;

attracting the distinct phase toward the collection surface;

disintegrating said distinct phase in said high intensity region;

collecting the magnetic component of the disintegrated distinct phase upon the collection surface when the distinct phase disintegrates; and removing the non-magnetic component of the disintegrated distinct phase away from the collection surface, thereby separating said at least one target substance from at least one non-target substance.

2. A method of separating at least one target substance from at least one non-target substance in a test fluid, comprising the steps of:

mixing the test fluid with a quantity of first and second magnetic particles to produce a suspension comprising a magnetic component and a non-magnetic component, wherein the magnetic component comprises first magnetic particles bound to said at least one target substance through at least one substance on the surface of the first magnetic particles which directly or indirectly binds to said target substance and second magnetic particles which possess properties necessary for the formation of a phase which contains both the magnetic and non-magnetic components and which is distinct from a magnetically inert fluid phase of a liquid system in which the separation of target substance occurs, and the non-magnetic component comprises the remainder of the test fluid, including the non-target substance;

establishing the magnetically inert fluid phase in a container having a collection surface therein;

introducing said suspension into the container as a stable phase which is distinct from the magnetically inert phase, to confine the magnetic and non-magnetic components of the suspension within the distinct phase;

generating in the container, a gradient magnetic field having a region of sufficiently high intensity adjacent to the collection surface to cause disintegration of the distinct phase into its constituent magnetic and non-magnetic components;

attracting the distinct phase toward the collection surface;

disintegrating said distinct phase in said high intensity region;

collecting the magnetic component of the disintegrated distinct phase upon the collection surface when the distinct phase disintegrates; and removing the non-magnetic component of the disintegrated distinct phase away from the collection surface, thereby separating said at least one target substance from at least one non-target substance.

3. The method of claim 1 or 2 wherein said introducing step includes conducting a flow of said suspension into said container on a continuous basis.

4. The method of claim 1 or 2, wherein said substance on the surface of the magnetic particles directly binds to said target substance.

5. The method of claim 1 or 2, wherein said substance on the surface of the magnetic particles is a capture agent which binds to at least one binding partner for said at least one target substance and said mixing step includes:

contacting said target substance with said binding partner and said capture agent-bearing magnetic particles thereby indirectly binding said target substance to said magnetic particles.

6. The method of claim 5, wherein each said binding partner binds to more than one target substance.

7. The method of claim 5, wherein each said capture agent binds to more than one binding partner.

8. The method of claim 1 or 2, wherein said establishing step comprises:

introducing an initial quantity of said suspension into said container;

separating the magnetic component of said initial quantity from the non-magnetic component thereof;

collecting the magnetic component of said initial quantity upon a collection surface within said container; and maintaining said non-magnetic component of said initial quantity in said container to form said magnetically inert fluid.

9. The method of claim 8, wherein the step of introducing said initial quantity is conducted according to a first flow rate, said step of introducing said suspension into said container to form a distinct phase is conducted according to a second flow rate, and said second flow rate is greater than said first flow rate.

10. The method of claim 1 or 2 wherein said introducing step includes conducting a flow of said suspension into said container and controlling turbulence in the suspension relative to the magnetically inert fluid to maintain integrity of the distinct phase.

11. The method of claim 10 wherein said controlling of turbulence includes conducting said flow of the suspension into the container in contact with a hydrodynamic damping structure.

12. The method of claim 1 or 2, comprising retrieving at least one of said magnetic component and said non-magnetic component of said disintegrated phase for recovery of at least one of said target substance and said non-target substance, respectively.

13. The method of claim 12, wherein said retrieving step includes receiving a flow of said non-magnetic component into a collection vessel.

14. The method of claim 12, wherein said retrieving of said magnetic component includes:

removing said magnetic field from said container;

resuspending said magnetic particles within said container;

conducting a flow of wash fluid through said container to remove said resuspended magnetic particles from within said container; and receiving said resuspended magnetic particles into a collection vessel.

15. The method of claim 14 wherein said wash fluid has a higher viscosity than said magnetically inert fluid.

16. The method of claim 1 or 2, wherein said at least one target substance is either at least one biological substance of interest or at least one other biological substance and said at least one non-target substance is the other of said at least one biological substance of interest or said at least one other biological substance.

17. The method of claim 16, wherein said substance on the surface of the magnetic particles directly binds to said target substance.

18. The method of claim 16, wherein said substance on the surface of the magnetic particles is a capture agent which binds to at least one binding partner for said target substance and said mixing step includes:

contacting said target substance with said binding partner and said capture agent-bearing magnetic particles thereby indirectly binding said target substance to said magnetic particles.

19. The method of claim 18, wherein each said capture agent binds to more than one binding partner.

20. The method of claim 16, wherein each said binding partner binds to more than one target substance.

21. The method of claim 16, wherein said introducing step includes conducting a flow of said suspension into the container on a continuous basis.

22. The method of claim 16, comprising retrieving at least one of said magnetic component and said non-magnetic component of said disintegrated phase for recovery of at least one of said target substance and said non-target substance, respectively.

23. The method of claim 16, wherein said separating of at least one biological substance of interest from at least one other biological substance in a test fluid comprises purging a test fluid of at least one undesired biological substance, wherein:

said undesired biological substance is a target substance; and said removing step further comprises retrieving said separated non-magnetic component of said disintegrated phase, to produce a sample from said test fluid, purged of said undesired biological substance.

24. The method of claim 23, wherein said undesired biological substance is selected from the group consisting of malignant cells, bacteria, fungi, viruses, microbial parasites, proteins, peptides and nucleic acids.

25. The method of claim 16, wherein said biological substance of interest and said other biological substance are selected from the group consisting of eucaryotic cells, procaryotic cells, subcellular organelles, viruses, proteins, peptides, nucleic acids, carbohydrates, and complex molecules comprising a combination of at least two of nucleic acids, proteins, lipids and carbohydrates.

26. The method of claim 25, wherein said biological substance of interest and said other biological substance comprise eucaryotic cells, said characteristic determinant comprises an antigen of said eucaryotic cells, and said binding partner comprises an antibody which binds to said antigen.

27. The method of claim 26, wherein said separating of at least one biological substance of interest from at least one other biological substance in a test fluid comprises enriching at least one cell type of interest from a mixed population of cell types, wherein:

said cell type of interest is a non-target substance and at least one of said mixed population of cell types is a target substance; and said removing step further comprises retrieving said separated non-magnetic component of said disintegrated phase, to produce a sample enriched for said cell type of interest.

28. The method of claim 27 wherein said at least one of said mixed population of cell types is malignant cells.

29. The method of claim 27, wherein said cell type of interest comprises less than about 10% of said mixed cell population.

30. The method of claim 29, wherein said cell type of interest comprises hematopoietic progenitor cells and said test fluid is selected from the group consisting of bone marrow and peripheral blood.

31. The method of claim 29, wherein said cell type of interest comprises fetal cells and said test fluid comprises fetal cells and maternal cells.

32. The method of claim 29, wherein said cell type of interest comprises genetically altered cells and said test fluid is selected from the group consisting of culture medium and a biological fluid.

33. The method of claim 26, wherein said separating of at least one biological substance of interest from at least one other biological substance in a test fluid comprises enriching at least one cell type of interest from a mixed population of cell types, wherein:

said cell type of interest is a target substance; and said removing step further comprises retrieving said separated magnetic component of said disintegrated phase, to produce a sample enriched for said cell type of interest.

34. The method of claim 33, comprising disassociating said cell type of interest from said retrieved magnetic component of said disintegrated phase.

35. The method of claim 33, wherein said cell type of interest comprises less than about 3% of said mixed cell population.

36. The method of claim 35, wherein said cell type of interest comprises hematopoietic progenitor cells and said test fluid is selected from the group consisting of bone marrow and peripheral blood.

37. The method of claim 35, wherein said cell type of interest comprises fetal cells and said test fluid comprises fetal cells and maternal cells.

38. The method of claim 35, wherein said cell type of interest comprises genetically altered cells and said test fluid is selected from the group consisting of culture medium and a biological fluid.

39. A method of controlling the movement of a substance within a magnetically inert fluid medium, comprising:

mixing said substance with a quantity of magnetic particles which possess properties necessary for the formation of a phase which is distinct from and stable in said magnetically inert fluid medium to form a suspension;

introducing said suspension into said fluid medium as a distinct phase from said fluid medium;

applying a magnetic field to the fluid medium, said magnetic field having a gradient within said fluid medium sufficient to attract said distinct phase and having an intensity that is sufficiently low to prevent disruption of said distinct phase; and altering the position of said magnetic field within said fluid medium to effect a desired movement of said distinct phase therein.

* * * * *